United States Patent [19]

Wilson et al.

[11] Patent Number: 5,281,621

[45] Date of Patent: * Jan. 25, 1994

[54] USE OF KETONE, ALCOHOL AND SCHIFF BASE-CONTAINING COMPOSITIONS FOR REPELLING BLOOD FEEDING ARTHROPODS AND APPARATUS FOR DETERMINING REPELLENCY AND ATTRACTANCY OF SEMIOCHEMICALS AGAINST AND FOR BLOOD FEEDING ARTHROPODS

[75] Inventors: Richard A. Wilson, Westfield; Braja D. Mookherjee, Holmdel, both of N.J.; Jerry F. Butler, Gainesville, Fla.; Eleanor Fox, New York; Vincent F. Kuczinski, Staten Island, both of N.Y.

[73] Assignees: International Flavors & Fragrances Inc., New York, N.Y.; The University of Florida, Gainesville, Fla.

[*] Notice: The portion of the term of this patent subsequent to Jun. 30, 2009 has been disclaimed.

[21] Appl. No.: 982,374

[22] Filed: Nov. 25, 1992

Related U.S. Application Data

[60] Continuation of Ser. No. 789,695, Nov. 8, 1991, abandoned, which is a division of Ser. No. 643,206, Jan. 18, 1991, Pat. No. 5,126,369.

[51] Int. Cl.$^5$ ............... A01N 43/16; A01N 37/10
[52] U.S. Cl. .................. 514/459; 514/521; 514/522; 514/535; 514/537; 514/919; 424/DIG. 10
[58] Field of Search ............ 514/459, 521, 522, 535, 514/537, 919; 424/DIG. 10

[56] References Cited

U.S. PATENT DOCUMENTS

| | | | |
|---|---|---|---|
| 4,380,674 | 4/1983 | Boden | 568/417 |
| 4,517,990 | 5/1985 | Boden | 131/276 |
| 4,775,720 | 10/1988 | Mookherjee et al. | 549/330 |
| 4,839,083 | 6/1989 | Mookherjee et al. | 512/8 |

*Primary Examiner*—Allen J. Robinson
*Assistant Examiner*—John D. Pak

*Attorney, Agent, or Firm*—Arthur L. Liberman

[57] ABSTRACT

Described is a process for repelling house flies and mosquitoes from a user of soap comprising the steps of:
(i) forming an insect repelling soap consisting essentially of a soap base and in intimate contact with the soap base an insect repellent quantity and concentration of a mixture of compounds defined according to the structures:

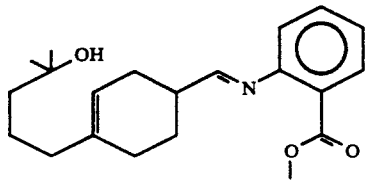

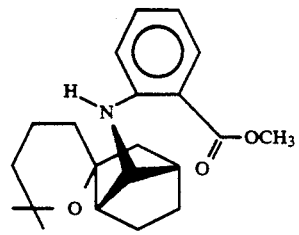

and

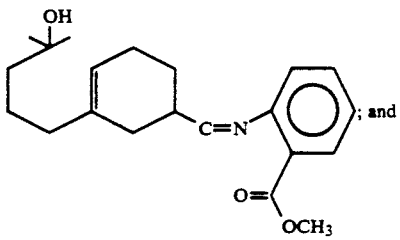

(ii) applying the thus-formed insect repellent soap to a user in a sufficient quantity to repel insects from the user.

1 Claim, 13 Drawing Sheets

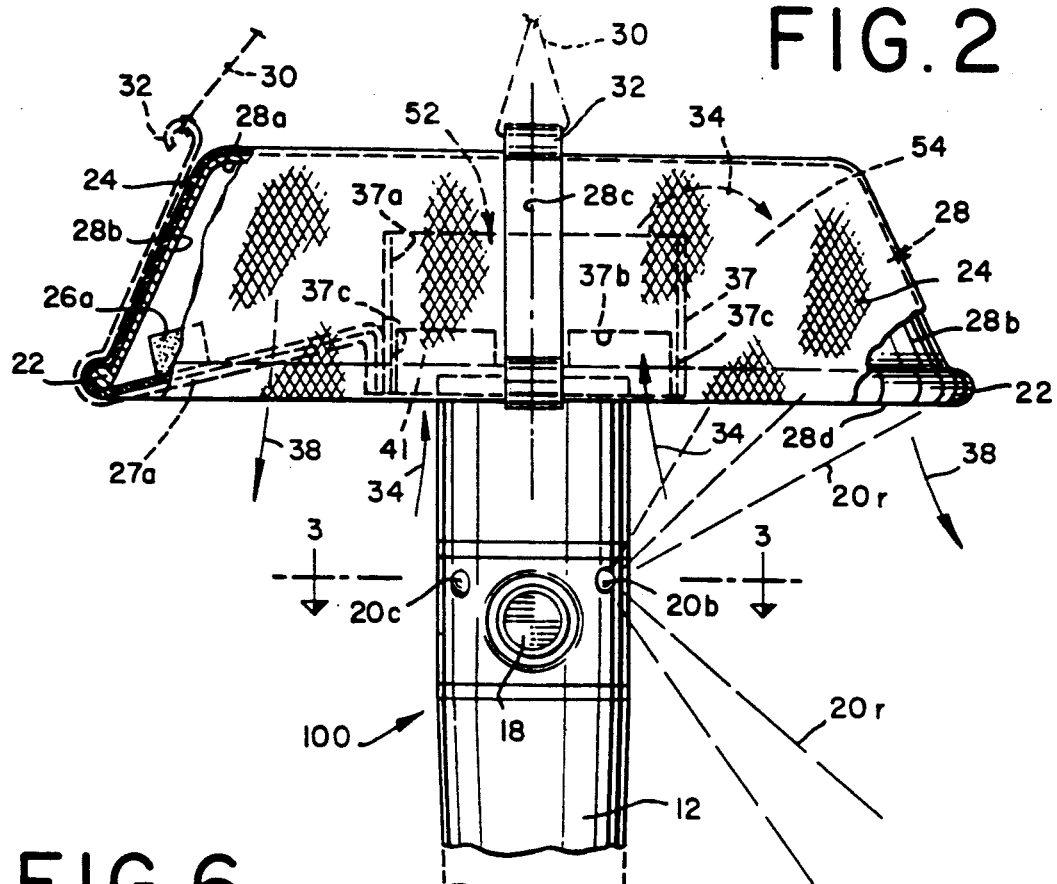
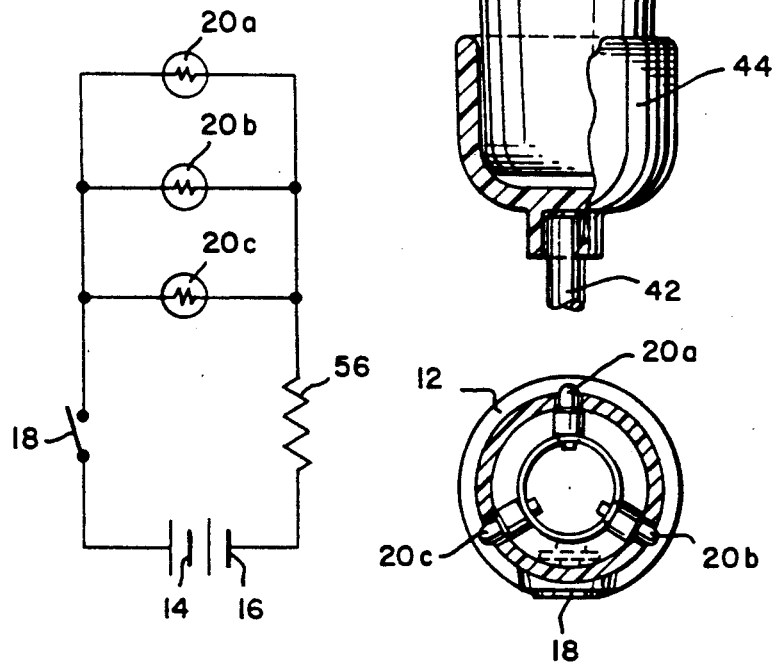

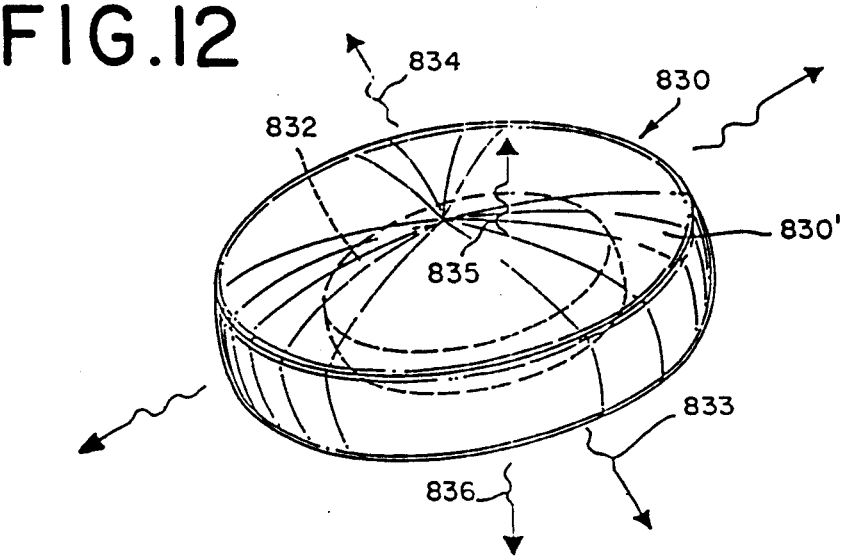
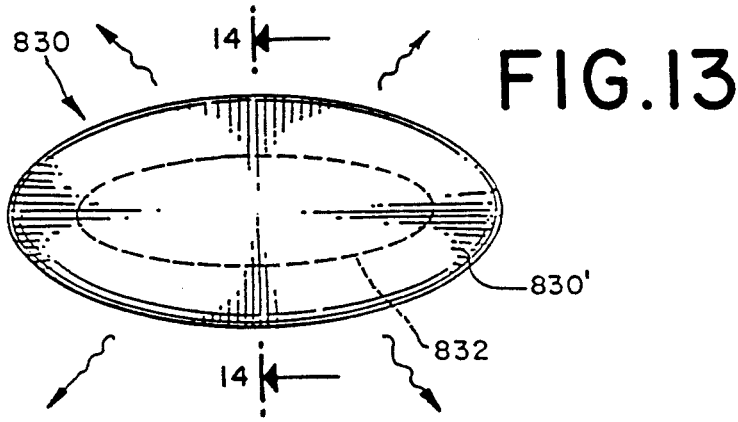
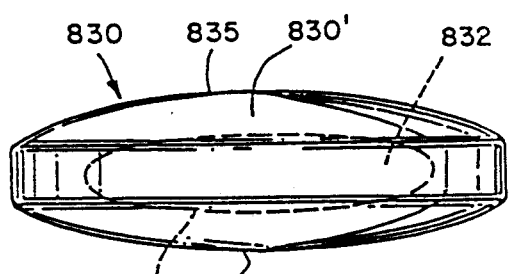
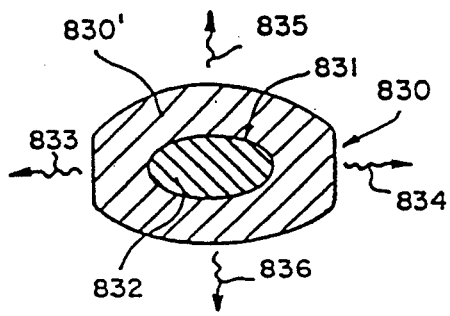

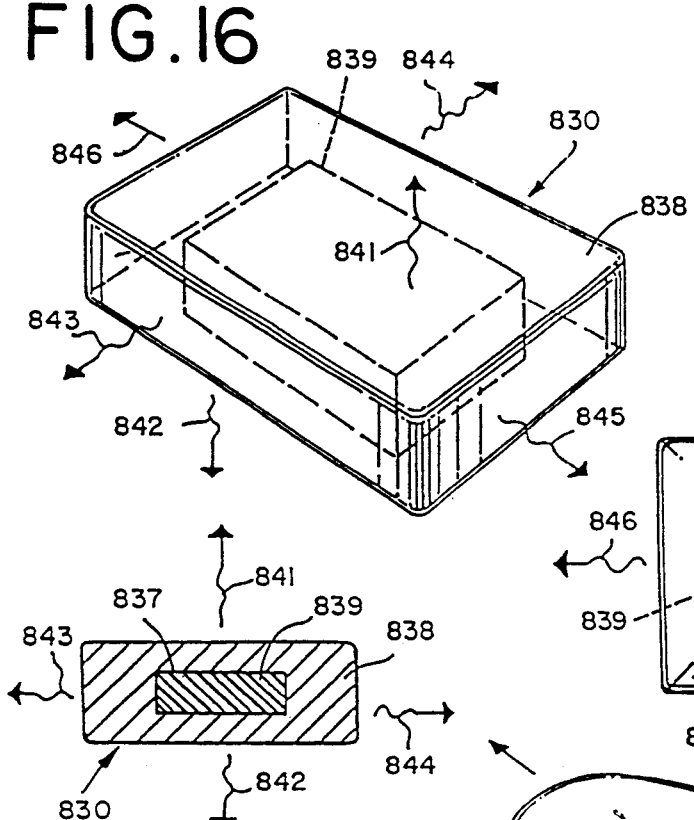
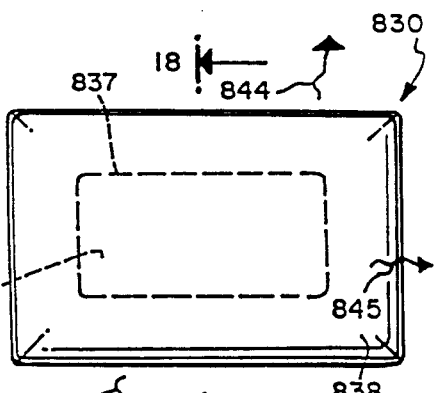
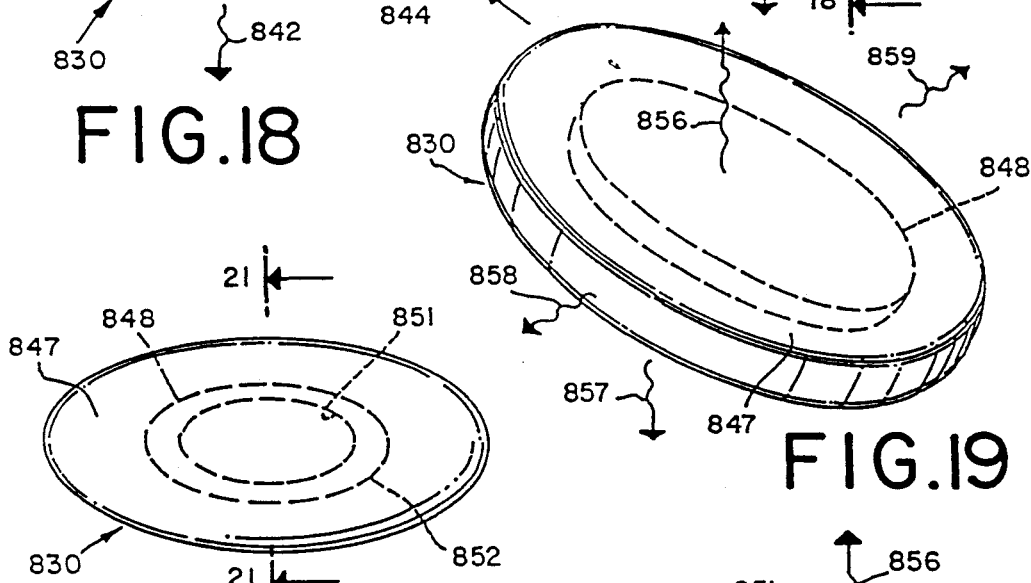
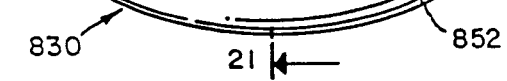
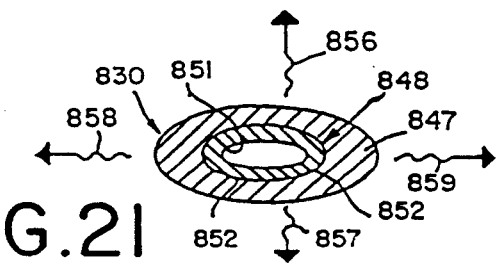

USE OF KETONE, ALCOHOL AND SCHIFF BASE-CONTAINING COMPOSITIONS FOR REPELLING BLOOD FEEDING ARTHROPODS AND APPARATUS FOR DETERMINING REPELLENCY AND ATTRACTANCY OF SEMIOCHEMICALS AGAINST AND FOR BLOOD FEEDING ARTHROPODS

This is a continuation of application Ser. No. 789,695, filed Nov. 8, 1991, now abandoned, which is a divisional of application Ser. No. 643,206 as originally filed on Jan. 18, 1991, now U.S. Pat. No. 5,126,369 issued on Jun. 30, 1992.

BACKGROUND OF THE INVENTION

Our invention relates to the use of the ketone composition, KOAVONE®, the alcohol, KOAVOL DH® and the schiff base, LYRAME® for repelling blood feeding arthropods, species of mosquitoes, houseflies, and gnats, as well as apparatus for determining repellency and attractancy of semiochemicals such as the aforementioned ketone alcohol and schiff base against and for such blood feeding arthropods.

Ketones and alcohols are known for repelling insects and the prior art contains many references pertaining to same. Thus, the use of 1-nonen-3-ol as a repellent is disclosed in U.S. Pat. No. 4,759,228 issued on Jul. 26, 1988, as a repellent for houseflies (*Musca domestica* L. (Diptera Muscidae)). Other ketones and an alcohol are disclosed in repelling mosquitoes (*Aedes aegypti*) as well as houseflies (*Musca domestica* L. (Diptera Muscidae)), in application for U.S. patent, Ser. No. 589,016 filed on Sep. 27, 1990.

Nothing in the prior art, however, sets forth the unexpected, unobvious and advantageous properties of the ketone, alcohol and schiff base of our invention so useful in repelling the species of insects set forth herein.

The prior art is replete with references showing various traps for insects, including said U.S. Pat. No. 4,759,228, issued on Jul. 26, 1988. Other prior art showing such insect traps is:

Griffiths and Bowman, Acarology VI, Volume 2, published by Ellis Horwood Limited §15.5., "Sampling techniques for burrow-dwelling ticks in reference to potential African swine fever virus vectors", (Butler, et al)

Garcia, R., (1962), Ann. Entomol. Soc. Amer., 55 605–606.

Garcia, R., (1965), Amer. J. Trop. Med. Hyg., 14 1090–1093.

Hair, J. A., Hoch, A. L., Barker, R. W., & Semtner, P. J, (1972), J. Med. Entomol., 9 153–155.

Holscher, K. H. Gearhart, H. L., & Barker, R. W., (1980) Ann. Entomol. Soc. Amer., 73 288–292.

Koch, H. G. & McNew, R. W., (1981), Ann. Entomol. Soc. Amer., 74, 498–500.

Nothing in the prior art sets forth the trap of our invention.

SUMMARY OF THE INVENTION

Our invention is directed to a semiochemical field trap for blood feeding arthropods, which has the capability of causing determination of repellency and attractancy of semiochemicals against and for blood feeding arthropods. The field trap comprises:

(1) An upright vertically disposed first hollow outer housing having substantially rigid arthropod-impermeable first side walls, an upper arthropod-impermeable horizontal surface substantially entirely contiguous with said first side walls, and a substantially entirely open bottom having a substantially horizontal plane substantially perpendicular to the vertical axis of said first hollow outer housing; (for example, such a first hollow outer housing can be a hollow frustum of a cone or a pyramid fabricated from such a material as aluminum);

(2) Located along an axis substantially perpendicular to the horizontal plane of the substantially entirely open bottom of said first outer housing, substantially parallel to the vertical axis of said fist hollow housing and within said first hollow housing, a second inner hollow housing having a hollow interior, opposite open upper first and lower second ends, vertically-disposed rigid arthropod-impermeable side walls, and a longitudinal dimension extending between the two ends, said upper first end being at a substantial distance below said upper substantially horizontal surface of said first outer housing (for example, the second inner hollow housing can be an open-ended cylinder fabricated of impermeable tin or aluminum);

(3) Extending outwardly from the substantially vertically disposed side walls of the second inner hollow housing to the side walls of the first hollow outer housing at an angle of from about −5° up to about −40°, measured downwardly from the substantially horizontal plane of the open bottom of the first hollow outer housing, substantially rigid rib components (for example, fabricated from steel, stainless steel or iron) which enable the fixed positioning of the inner hollow housing with respect to the positioning of and within said outer hollow housing (the preferred angle being about −10°);

(4) Completely encompassingly traversing in a substantially tight fitting manner the area between (i) the first side walls of said first outer hollow housing and (ii) the second side walls of said second inner hollow housing along the directional vectors of said rib components and in a curvilinear plane below and substantially contiguous to said rib components, a continuous substantially macroporous mesh substance having such a mesh size as to be impenetrable by arthropods sought to be entrapped, but pervious to gas and liquid and, in addition, radiation transmittable, and capable of supporting a matrix article containing sustainably releasable semiochemical (for example, nylon mesh having a mesh size in lines per inch of from about 10 up to about 200);

(5) Optionally, at least one semiochemical-containing matrix comprising a porous containment agent (e.g., polyethylene, polypropylene, a polyamid, a polyurethane or the like) containing in the interstices thereof at least one semiochemical sustainably releasable therefrom, (e.g., one or more of the ketone, alcohol or schiff base of our invention) located on the upper surface of said macroporous mesh substance (e.g., nylon mesh);

(6) A substantially vertically disposed drive shaft supported for rotary motion about its axis, extending from below and into the hollow interior of the second inner hollow housing along the longitudinal dimension thereof;

(7) Motor means connected to a first lower end of the drive shaft for rotating the drive shaft about its axis;

(8) Air flow creation means (e.g., a propeller) attached to a second upper end of the drive shaft, being of such a design whereby the rotation of the drive shaft directly causes the rotation of the air flow creation means and induces the flow of air from beneath the second inner hollow housing upwardly into the three space within the first outer hollow housing (e.g., the hollow frustum of a cone) between the outer side wall of the second inner hollow housing (e.g., the open ended cylinder) and the inner side wall of the first outer hollow housing (e.g., the hollow frustum of the cone);

(9) Optionally, radiation emission means (e.g., an infrared light source or a bright green light source) for emission of radiation of a specific wave length or of a range of wave lengths outwardly from the apparatus located in the vicinity of the lower portion of the second inner hollow housing below the location of the rib components;

(10) Power supply means (e.g., flashlight batteries) associated with the trap causing the radiation emission means to generate radiation and energizing the motor means;

whereby arthropods (e.g., the listed mosquitoes, houseflies and gnats) in the vicinity of the trap are attracted by the radiation to a location so close to the trap that in the event that an attracting semiochemical in the matrix is detected by the arthropods, the arthropods will enter the air stream created by the air flow creation means and be carried into the 3-space within the first hollow outer housing between the outer side wall of the second inner hollow housing and the inner side wall of the first outer hollow housing. As stated above, it is optional in the operation of the trap to include the semiochemical-containing matrix as well as the radiation emission means. The trap of our invention is intended to test not only semiochemicals (e.g., insect attractants and repellents) and the attractancy or repellency of various types of radiation such as infrared light, but may also be used to test the attractancy or air as well as gases. Thus, the trap of our invention may also include:

(11) A carbon dioxide gas supply means for supplying gaseous carbon dioxide to the proximity of the lower portion of the second inner hollow housing below the location of the rib components simultaneously with the operation of the power supply means. The carbon dioxide itself has the ability to attract various types of insects. It is our intention to cover the trap including and not including the carbon dioxide gas supply means.

Preferably, there should be approximately 0.25 inches–0.50 inches clearance between the top of the second inner housing (e.g., cylinder) and the bottom of the upper arthropod-impermeable horizontal surface of the first hollow outer housing. Furthermore, the air flow creation means (e.g., propeller) should preferably protude 0.125 inches–0.25 inches from the bottom of the second inner hollow housing (e.g., open-ended metal cylinder).

It is preferable when using the radiation emission means, to use infrared light. Control experiments are preferably run using carbon dioxide with the use of infrared radiation lights and without the use of infrared radiation lights. However, experiments using the trap may also be carried out with other lights such as bright green lights. In both cases, the radiation emission means utilize the circuit, preferably, of FIG. 5. An example of the green light being used, is one manufactured by the Marktech International Corporation of Menands, N.Y., Catalog Part No. MT300-CUG (T-1.75 water clear ultra-bright green light emitting diode lamp). When using infrared radiation means, it is preferable to utilize a gallium arsenide infrared light emitting diode such as Model MTE 1080 gallium arsenide emitter manufactured by Marktech of 120 Broadway, Menands, N.Y. 12204.

When preparing the semiochemical matrix which is preferably a block, 10 microliters of test material, e.g., the ketone alcohol or schiff base used in our invention are soaked into a 9 mm×9 mm×9 mm block. The carbon dixode supply source is most conveniently dry ice placed in a "zippered" bag (with a tygon tubing outlet). The dry ice is placed in a zippered bag and the bag is then placed in an insulated ice chest. Preferably between between 4 and 5 kilograms of dry ice is used, preferably in the form of pellets or blocks.

On placing the trap in the test area, the motor means is engaged with the power supply means, preferably, simultaneously with the engagement of the radiation means with the power supply means. Thus at the instant that the trap is commenced to be in use, the air flow creation means (e.g., the propeller) begins its rotation simultaneously with the radiation means being energized and with the motor means being energized. Thus, arthropods, e.g., mosquitoes, houseflies and gnats as set forth supra in the vicinity of the trap are attracted by the radiation to a location so close to the trap that in the event that an attracting semiochemical in the matrix is detected by the arthropods, the arthropods will enter the air stream created by the air flow creation means, e.g., propeller and be carried into the 3-space within the first hollow outer housing between the outer side wall of the second inner hollow housing and the inner side wall of the first outer hollow housing. Once within the trap the arthropods will not escape in view of the fact that they are in the vicinity of the carbon dioxide being emitted by the carbon dioxide supply source and they are in the vicinity of the radiation emitted by the radiation emission means and are attracted thereto. Furthermore, the rotation of the air flow creation means prevents the arthropods from leaving the 3-space within the first hollow outer housing where they are trapped. The traps are usually run for a period of from about 36 hours to about 40 hours. They are set up in usually four rows of four, approximately 60 feet apart.

Preferably, the mesh size of the nylon used for the continuous substantially macroporous mesh substance of (4) of the trap should range from about 10 up to about 200 lines per inch and thus, for example, may be 20/6 T-66 textured nylon or 70/32 polyester (e.g., a polymer of phthalic anhydride and ethylene glycol).

Our invention is also directed to a method for repelling at least one of the insect species:
(a) *Musca domestica* L. (Diptera Muscidae);
(b) *Aedes aegypti*;
(c) *Aedes albopictus*;
(d) Anopheles spp.;
(e) *Coquillettidia perturbans*;
(f) Culiseta spp.;
(g) Culex spp.;
(h) Psorophora spp.;
(i) Culicoides spp.; and/or
(j) Lutzomyia spp.
for a finite period of time from a three dimensional space comprising the step of exposing said three dimensional space to to a:
(a) *Musca domestica* L. (Diptera Muscidae);
(b) *Aedes aegypti*;

(c) *Aedes albopictus;*
(d) Anopheles spp.;
(e) *Coquillettidia perturbans;*
(f) Culiseta spp.
(g) Culex spp.;
(h) Psorophora spp.;
(i) Culicoides spp.; and/or
(j) Lutzomyia spp.

repelling concentration and quantity of a composition of matter which may be in the alternative:

(a) LYRAME ® a mixture of compounds defined according to the generic structure:

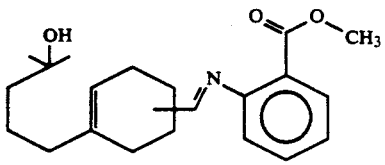

(b) KOAVOL DH ® defined according to the structure:

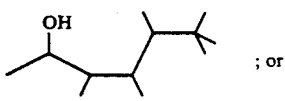; or (c) KOAVONE ® consisting essentially of a mixture of compounds defined according to the generic structure:

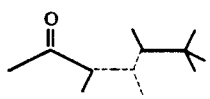

wherein in each of the compounds of the mixture, one of the dashed lines represents a carbon-carbon double bond and each of the other of the dashed lines represents a carbon-carbon single bond.

Our invention is also directed to an insect repelling soap which can repel any of the species of insects set forth above comprising a soap base and in intimate contact therewith, at least one insect repellent composition of matter which may be in the alternative:

(a) LYRAME ®;
(b) KOAVOL DH ®; or
(c) KOAVONE ®.

More specifically, the mixture of compounds defined according to the structure:

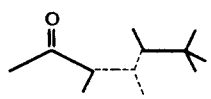

is actually a mixture of the compounds having the structures:

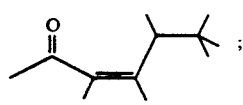

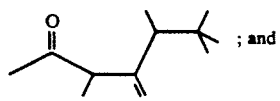; and

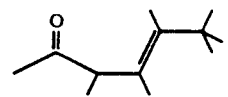

This mixture of compounds may be produced according to, for example, the teachings of U.S. Pat. No. 4,380,674 issued on Apr. 19, 1983, particularly according to Example Y(A) or Example Y(B) at Columns 34, 35 and 36 of said U.S. Pat. No. 4,380,674.

Furthermore, the compound having the structure:

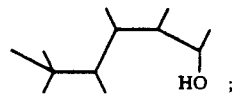

the "alcohol" of our invention may be prepared according to the teachings of U.S. Pat. No. 4,517,990 issued on May 21, 1985, particularly in accordance with Example III at Column 20 of said U.S. Pat. No. 4,517,990.

The schiff base of our invention represented by the structure:

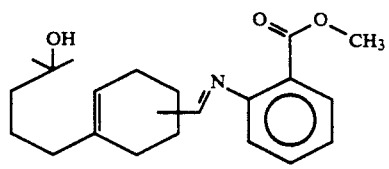

is actually a mixture of the compounds having the structures:

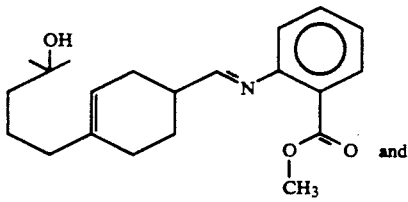

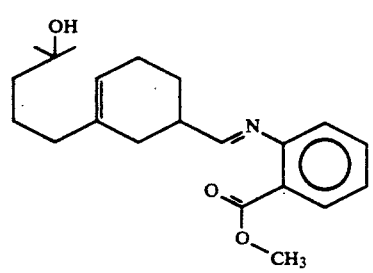

and may be prepared in accordance with the teachings or U.S. Pat. No. 4,775,720 issued on Oct. 4, 1988, particularly at Example VI, Columns 65, 66, 67, 68, 69 and 70 of said U.S. Pat. No. 4,775,720. This mixture may additionally contain the compound having the structure:

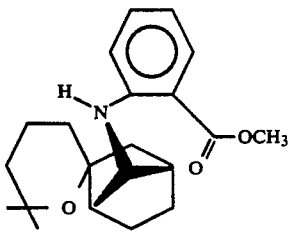

whose NMR spectrum is shown in FIG. 14 of said U.S. Pat. No. 4,775,720. Thus our invention is directed not only to the use of mixtures of the compound defined according to the structure:

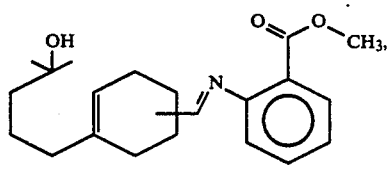

but also mixtures of compounds having the structures:

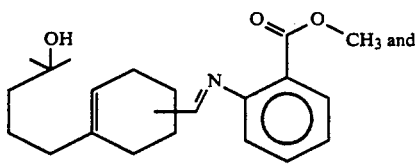

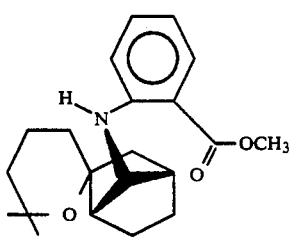

Another aspect of our invention relates to the formation of the insect repelling articles, that is articles containing at least one of:
(a) KOAVONE ®;
(b) KOAVOL DH ®; or
(c) LYRAME ®
useful for the repelling of the insect species:
(a) *Musca domestica* L. (Diptera Muscidae);
(b) *Aedes aegypti;*
(c) *Aedes albopictus;*
(d) *Anopheles* spp.;
(e) *Coquillettidia perturbans;*
(f) *Culiseta* spp.;
(g) *Culex* spp.;
(h) *Psorophora* spp.;
(i) *Culicoides* spp.; and/or
(j) *Lutzomyia* spp.
in combination with compatible polymers, e.g., high density polyethylene or low density polyethylene. Thus, one aspect of our invention provides a process for forming semiochemical-containing polymeric particles such as foam polymeric pellets which include a relatively high concentration of at least one of: (a) KOAVONE ®, (b) KOAVOL DH ®, or (c) LYRAME ®.

Thus, one aspect of our invention relates to the formation of semiochemical polymeric pellets by means of introduction into a single screw or twin screw extruder of, in series, thermoplastic polymer followed by semiochemical which is compatible with the thermoplastic polymer, in turn (optionally) followed by introduction of a gaseous blowing agent or blowing agent which will produce a gas which is inert to the polymer and to the KOAVONE ®, KOAVOL DH ® or LYRAME ® semiochemical previously introduced into the extruder.

The advantages of using a foamed polymeric particle are multiple, to wit: improved handling, greater retention of the semiochemical, KOAVOL DH ®, KOAVONE ® or LYRAME ®, when not in use; greater length of time during which release of the semiochemical from the polymer is at "steady state" or "zero order".

The nature of the extruder utilized in the process of our invention to form the polymeric semiochemical-containing polymer particles of our invention may be be either single screw or double screw. Thus, the types of extruder that can be used are disclosed at pages 246–257 and 332–349 of the Modern Plastics Encyclopedia, 1982–1983, published by the McGraw-Hill Publishing Company, the disclosure of which is incorporated by reference herein. More specifically, examples of extruders which are usable in carrying out one of the processes of our invention (with modification for introduction of the semiochemical) downstream from the introduction of the polymer and with further modification that the gaseous blowing agent is introduced still further downstream from a point of introduction of the semiochemical, e.g., KOAVONE ®, KOAVOL DH ®, and/or LYRAME ® are as follows:

1. The Welex "Super Twinch" 3.5″ extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kans. 67277;
3. Modified Sterling model 4000 and 5000 series extruder manufactured by Sterling Extruder Corporation of 901 Durham Avenue, South Plainfield, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder manufactured by the Werner & Pfleiderer Corporation of 6763 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff single screw, twin screw, or foam extrusion equipment manufactured by Berstorff Corporation, P.O. Box 240357, 8200-A Arrowridge Blvd., Charlotte, N.C. 28224.

In producing the semiochemical (e.g., KOAVONE ®, KOAVOL DH ® or LYRAME ®) polymer particles of our invention, various polymers may be utilized, for example, low density polyethylene, high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ethylene and vinyl acetate. Preferred co-polymers are polyethylene-vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed by the E. I. duPont de Nemours Company under the tradename "ELVAX®" and by the Arco Polymer Division under the trademark "DYLAND®" and by the Exxon Corporation of Linden, N.J. under the trademark "DEXXON®". Ethylene/ethyl acrylate co-polymers are marketed by Union Carbide Corporation under the tradename "EEA RESINS®".

The polymer is added to the single screw or twin screw extruder at a feed rate in the range of from about 80 up to about 300 pounds per hour while maintaining the temperature of the extruder between about 160° and about 240° C. If the polymer or co-polymer powder is added to the extruder at a reference "barrel segment", then the KOAVONE®, KOAVOL DH® or LYRAME® is added to the extruder under pressure downstream from the addition point of the polymer at 1 or more of "barrel segments" S-2, S-3, S-4, S-5, S-6, S-7, S-8 or S-9 (referring to FIG. 7 briefly described, supra and described in detail, infra.

The proportion of KOAVONE®, KOAVOL DH® or LYRAME® resin can vary from small but effective amounts on the order of about 1% of the weight of resin body up to about 45% by weight of the resin body. In general it is preferred to use between about 5% up to about 30% based on the weight of the resin body of KOAVONE®, KOAVOL DH® or LYRAME®. This is an optimum amount balancing the proportion of KOAVONE®, KOAVOL DH® or LYRAME® against the time period over which the article emits the KOAVONE®, KOAVOL DH® or LYRAME® and against the tendency of the KOAVONE®, KOAVOL DH® or LYRAME® to "oil out". This "oiling out" is specifically avoided as a result of use of the foaming agent discussed, infra.

Various polymers are useful in the practice of our invention. Specific examples of polymers useful in the practice of our invention are as follows:

(a) DYLAN® brand of low density polyethylene DYLAN® is a trademark owned by the Atlantic Richfield Company of Los Angeles, Calif.;

(b) DYLITE® of expandable polystyrene compostions. DYLITE® is a trademark of the Atlantic Richfield Company of Los Angeles, Calif.

(c) SUPER DYLAN® is a high density polyethylene. SUPER DYLAN® is a trademark of the Atlantic Richfield Company of Los Angeles, Calif.;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated by reference herein;

(f) Polyene/alpha-olefin as exemplified and disclosed in U.S. Pat. No. 4,369,291, the specification for which is incorporated by reference herein;

(g) Poly-alpha-olefins as exemplified in Canadian Letters Pat. No. 1,137,069 issued on Dec. 7, 1982, the specification for which is incorporated by reference herein;

(h) Polymeric compositons as disclosed in Canadian Letters Pat. No. 1,137,068 issued on Dec. 7, 1982, the specification for which is incorporated by reference herein;

(i) Poly-alpha-olefins disclosed in Canadian Letters Pat No. 1,137,067, the specification for which is incorporated by reference herein;

(j) Polyolefins described in Canadian Letters Pat. No. 1,137,066, the specification for which is incorporated by reference herein;

(k) Polyethylene oxides as disclosed in Canadian Letters Pat. No. 1,137,065 issued on Dec. 7, 1982, the specification for which is incorporated by reference herein;

(l) Olefin polymers and co-polymers as disclosed in Canadian Letters Pat. No. 1,139,737, the disclosure of which is incorporated by refernce herein. Canadian Pat. No. 1,139,737 was issued on Jan. 18, 1983;

(m) Polyolefins disclosed in Canadian Letters Pat. No. 1,139,738, the disclosure of which is incorporated by reference herein. Canadian Pat. No. 1,139,738 was issued on Jan. 18, 1983;

(n) Chlorinated PVC as disclosed in Polymer 1982, 23 (7, Suppl.), 1051-6 abstracted at Chem. Abstracts 97:145570y, 1982;

(o) Polyepsilon caprolactone co-polymers made by means of alcohol initiated polymerization as disclosed in J. Polym. Sci. Polym. Chem. Ed., 1982, 20(2), pages 319-26, abstracted at chem. Abstracts, Volume 96:123625x, 1982;

(p) Styrene acrylonitrile co-polymers as disclosed in Diss. Abstracts, Int. B, 1982, 42(8), 3346 and abstracted at Chem. Abstracts 96:143750n (1982);

(q) Co-polymers of epsilon carprolactone with 1,4-butane diol as disclosed at Kauch. Rezine, 1982, (2),8-9, abstraced at Chem. Abstracts, Volume 96:182506g (1982);

(r) Polyesters as disclosed in U.S. Pat. No. 4,326,010, the specification for which is incorporated by reference herein;

(s) Chlorinated polyethylene as disclosed by Belorgey, et al., J. Polym. Sci. Polym. Phys. Ed., 1982, 20(2), 191-203;

(t) Plasticized polyepsilon caprolactone co-polymers containing dimethyl phthalate plasticizers as set forth in Japanese Pat. No. J81/147844, abstracted at Chem. Abstracts, Volume 96:69984y (1982), the specification for which is incorporated by reference herein;

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resisns wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

Downstream from the addition point of the KOAVONE®, KOAVOL DH® or LYRAME®, optionally, the gaseous or liquid containing blowing agent may be added (e.g., at barrel segments S-5, S-6, S-7, S-8, S-9 or S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed KOAVONE®, KOAVOL DH® or LYRAME® containing particle.

The feed rate range of KOAVONE®, KOAVOL DH® or LYRAME® may be between about 0.5% up to about 45% by weight of the polymer.

The die of the extruder may create rod, sheet film or ribbon. The resulting product may then, if desired, be pelletized to form KOAVONE®, KOAVOL DH® or LYRAME® containing polymer particles or the ribbon may be used "as-is" as a KOAVONE®, KOAVOL DH® or LYRAME® containing polymeric article of manufacture itself.

In addition to the optional gaseous blowing agents (which are necessarily "inert" gases), blowing agents may be added at the same point on the extruder which will create gaseous voids in the KOAVONE®, KOAVOL DH® or LYRAME® containing polymer articles of our invention and these "blowing agents" are well known to one having ordinary skill in the art.

Examples of such non-gaseous containing materials which yield gases on admixture with the polymer in the extruder but which are still inert to the insect attractant are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CFC_3$, $CF_2Cl_2$ $CH_3Cl$, $CH_2Cl_2$ separately or in admixture with one another as set forth in U.S. Pat. No. 3,758,425, column 4, lines 1–5, the specification for which is incorporated by reference herein;

(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specifications for which are incorporated herein by reference; and (iv) Azo bis(formamide); diazoaminobenzene; N,N'-dinitrosopentamethylene tetramine; N,N'-dimethyl-N,N'-dinitrosoterephthalamide; p,p'-oxy-bis(-benzene sulfonyl semicarbazide); azo bis-(isobutyronitrile); p,p'-oxybis(benzene sulfonyl hydrazide); p,p'-diphenyl-bis (sulfonyl hydrazide); benzene-sulfonyl hydrazide; m-benzene-bis (sulfonyl hydrazide) as more specifically described in U.S. Pat. No. 3,298,975 issued on Jan 17, 1967, the specification for which is incorporated by reference herein.

The resulting extruded (and if desired pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

In addition, our invention relates to candle body materials which on use are both insect repellent and perfuming and which contain KOAVONE®, KOAVOL DH® or LYRAME® in order to repel at least one of the insect species:

(a) *Musca domestica* L. (Diptera Muscidae);
(b) *Aedes aegypti;*
(c) *Aedes albopictus;*
(d) Anopheles spp.;
(e) *Coquillettidia perturbans;*
(f) Culiseta spp.;
(g) Culex spp.;
(h) Psorophora spp.;
(i) Culicoides spp.; and/or
(j) Lutzomyia spp.

The insect repellent-perfume compositions which form part of the candle body materials are within the following specifications:

(I) from 5 up to 100% by weight of an efficacious perfume/insect repellent composition consisting essentially of KOAVONE®, KOAVOL DH® and/or LYRAME®; and (II) from 0 up to 95% of a standard perfuming substance (not necessarily insect repellent) which may be one or a combination of the following materials:

the methyl ester of 2,5-dihydroxy-4,6-dimethyl benzoic acid;
dihydro myrcenol;
oakmoss absolute;
benzyl acetate;
geraniol;
isobornyl acetate;
citronellye acetate;
para-t-butyl phenyl isovaleraldehyde;
benzyl salicylate;
hexyl cinnamic aldehyde;
geranonitrile;
patchouli oil;
alpha-terpineol;
tetrahydromuguol;
phenyl ethyl alcohol;
cedrenal;
methyl ionone;
cinnamyl acetate;
benzyl benzoate;
L-Citronellal;
nerol;
geranyl formate;
geranyl acetate;
eugenol;
alpha Farnesene;

beta Farnesene;
citral;
n-Nonanal;
n-Octanal; and
trans, trans delta-damascone.

The foregoing formulae may require a solubilizing agent, e.g., the methyl ester of dihydroabietic acid (commercial name: HERCOLYN D ®), benzyl benzoate, isopropyl myristate and/or $C_{12}$–$C_{14}$ isoparaffin hydrocarbons.

The candle base composition can be standard paraffin wax, or it can be transparent or pastel shaded as more particularly described in U.S. Pat. No. 3,615,289 issued on Oct. 26, 1971 (the disclosure of which is incorporated by reference herein) and wherein the candle body comprises as the basic components a mixture of:

(i) a thermoplastic polyamide resin formed from linoleic acid polymerized with a polyamine compound;
(ii) an alkanol amide or alkanol amine; and
(iii) a stearic acid compound.

The weight of ratio of candle body: KOAVONE ®, KOAVOL DH ® or LYRAME ® perfumant substance of our invention may vary from about 0.8% up to about 10% with a range of from about 0.8% up to about 2.0% being preferred when no non-insect repelling perfume oil is used in conjunction with the KOAVONE ®, KOAVOL DH ® or LYRAME ®; and with a range of from about 1.5% up to about 10% by weight of the overall composition being preferred when a non-insect repelling perfume oil is used in conjunction with the KOAVONE ®, KOAVOL DH ® or LYRAME ®.

Specifically, the polyamide may be a "Versamid" resin which is a thermoplastic condensation product of polymerized linoleic acid with various polyamine compounds such as ethylene diamine, ethylene triamine and the like. Specific "Yersamid" compounds are "YERSAMID ® 900", "VERSAMID ® 930", "VERSAMID 940 ®, "VERSAMID ® 948", "YERSAMID ® 950" and "VERSAMID ® 1635". These compounds are products of the Henkel Chemical Corporation of Minneapolis, Minn.

Another substance required in the clear candle composition consists of about 20-55% by weight of an alkanol amine or alkanol amide prepared by the reaction of a fatty acid ester and amine whereby the ester and the amine are in substantially equal proportions, for example, compounds such as Barlol 12C2 (manufactured by the Barrid Chemical Company) a monoalkyl diethanolamine have 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. These stearic acid compounds serve as stabilizing agents which permit the ready incorporation of the insect repellent/perfumant compositions of our invention up to a level of approximately 5% (total proportion of perfume oil-insect repellent composition). They are carriers for the perfumant/insect repellent and may be used in a proportion of between 1 and 50% by weight of the composition although the preferable range is between 20 to 30%. In this connection it is possible to use up to about 10% by weight of perfumant/insect repellent if part of the formula is replaced by the material "Nevex 100", a product which is a coumarin-indene copolymer resin of very little unsaturation, manufactured by the Neville Chemical Company.

Rather than being a crystalline paraffin wax the candle base of our invention may be an oil gel that has as its base a light mineral oil, an inexpensive natural oil or a combination of such oils which oil gel has a non-greasy surface and feel and sufficient rigidity to be self-supporting at room temperatures. Such a gel is disclosed in U.S. Pat. No. 3,645,705 issued on Feb. 29, 1972, the disclosure of which is incorporated by reference herein. Such compositions of matter include:

(a) from about 35% up to about 85% by weight of an oil which is normally liquid at room temperature chosen from the group consisting of light mineral oil and natural oils having iodine values substantially within the range of 40–135;

(b) from about 7% up to about 40% by weight of a long chain polyamide having a molecular weight substantially within the range of 6000–9000 and a softening point substantially within the range of 18° C.–48° C.; and (c) from about 7% to about 30% of an alcohol selected from the group consisting of 8 to 12 carbon primary alcohols.

Such composition may additionally include from about 1% up to about 15% of a methyl ester; up to about 5% by weight of stearic acid and up to about 5% by weight of an oxidation inhibiting agent and up to about 5% by weight of an acid selected from the group consisting of dimer and trimer acids.

The following Tables I and II show the results of utilization of the olfactometer apparatus of FIG. 24 in testing for the attractancy or repellency of *Musca domestica* L. (Diptera Muscidae) and *Aedes aegypti*, using LYRAME ®, KOAVOL DH ®, and KOAVONE ®.

TABLE I

| COMPOSITION TESTED | AEDES AEGYPTI |||||||
|---|---|---|---|---|---|---|---|
| | INSECTS PER INTERVAL |||||||
| LYRAME ® | 0 | 12 | 3 | 2 | 0 | 0 | 1 |
| LYRAME ® | 0 | 34 | 0 | 0 | 0 | 0 | 0 |
| KOAVONE ® | 0 | 12 | 67 | 26 | 80 | 30 | 85 |
| KOAVOL DH ® | 0 | 62 | 69 | 91 | 87 | 47 | 3 |
| AIR | 0 | 233 | 382 | 376 | 295 | 331 | 151 |

TABLE II

| COMPOSITION TESTED | MUSCA DOMESTICA L. (DIPTERA MUSCIDAE) |||||||
|---|---|---|---|---|---|---|---|
| | INSECTS PER INTERVAL |||||||
| LYRAME ® | 0 | 46 | 55 | 12 | 12 | 13 | 3 |
| LYRAME ® | 0 | 3 | 4 | 0 | 1 | 0 | 0 |
| KOAVONE ® | 0 | 0 | 2 | 13 | 3 | 1 | 1 |
| KOAVOL DH ® | 0 | 16 | 16 | 26 | 15 | 41 | 52 |
| AIR | 0 | 153 | 463 | 133 | 293 | 167 | 94 |

DESCRIPTION OF THE DRAWINGS

FIG. 2 is a side elevation view of the semiochemical field trap for blood feeding arthropods of our invention.

FIG. 3 is a top sectional view of the semiochemical field trap for blood feeding arthropods of FIG. 2 looking along lines 3—3.

FIG. 6 is a schematic diagram of the electrical circuit setting forth the radiation emission means for emission of radiation of a specific wave length of or a range of wave lengths using power supply means, showing a switch, showing 3 light emitting diodes and showing a resistor.

FIG. 12 is a perspective view of an ellipsodially-shaped detergent tablet containing a solid core which includes fused foamed polymeric particles which contain insect repellents which can be one or more of the ketone, alcohol or schiff base of our invention and if desired also containing an additional polymer, e.g., polyethylene. The polymer particles may, if desired, also contain additional aromatizing agents.

FIG. 13 is the top view of the ellipsodially-shaped detergent tablet of FIG. 12.

FIG. 14 is a cut-away front view of the ellipsodially-shaped detergent tablet of FIG. 12 in the direction of the arrows in FIG. 13.

FIG. 15 is a side view of the ellipsodially-shaped detergent table of FIG. 13.

FIG. 16 is a perspective view of a rectangular parallelpiped shaped detergent tablet containing a rectangular parallelpiped shaped core comprising a major proportion of fused foam polymeric particles which contain insect repellent, (e.g., one or more of the ketone, alcohol or schiff base of our invention) and may or may not be aromatized and, if desired, an additional polymer which may or may not contain insect repellent compositions and which may or may not be aromatized.

FIG. 17 is a top view of the rectangular parallelpiped shaped detergent tablet of FIG. 16.

FIG. 18 is a cut-away front view of the rectangular parallelpiped shaped detergent tablet of FIG. 16 looking in the direction of the arrows in FIG. 17.

FIG. 19 is a perspective view of an ellipsoidally-shaped detergent tablet containing a hollow insect repellent agent (and, if desired, an aromatizing agent) containing core which includes fused foamed polymeric particles (the insect repellent and if desired the aroma imparting agent) is in the solid polymer and not in the void of the plastic core.

FIG. 20 is a top view of the ellipsoidally-shaped detergent table of FIG. 19.

FIG. 21 is a front cut-away view of the ellipsoidally-shaped detergent tablet of FIG. 19 looking in the direction of the arrows in FIG. 20, the core thereof being hollow and either containing an insect repellent material (and, if desired, an aroma imparting liquid) or in the alternative being a hollow core wherein the insect repellent material (and if desired, the aroma imparting material) is in the solid fused foamed polymeric particles which make up the core and wherein the void does not contain anything.

DETAILED DESCRIPTION OF THE DRAWINGS

Figure 1:
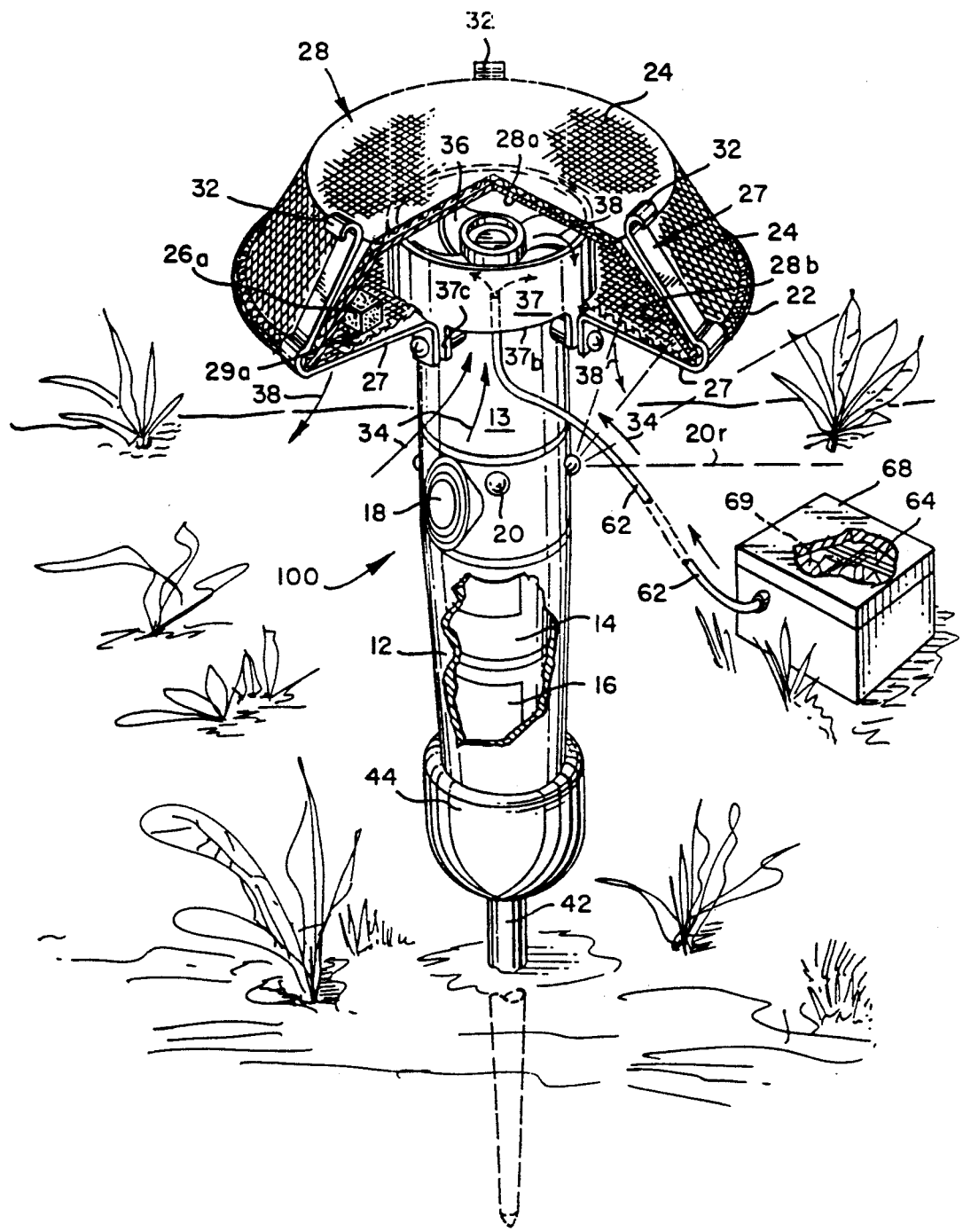
FIG. 1 is a cut-away perspective view of the semiochemical field trap for blood feeding arthropods of our invention.
Figure 4:
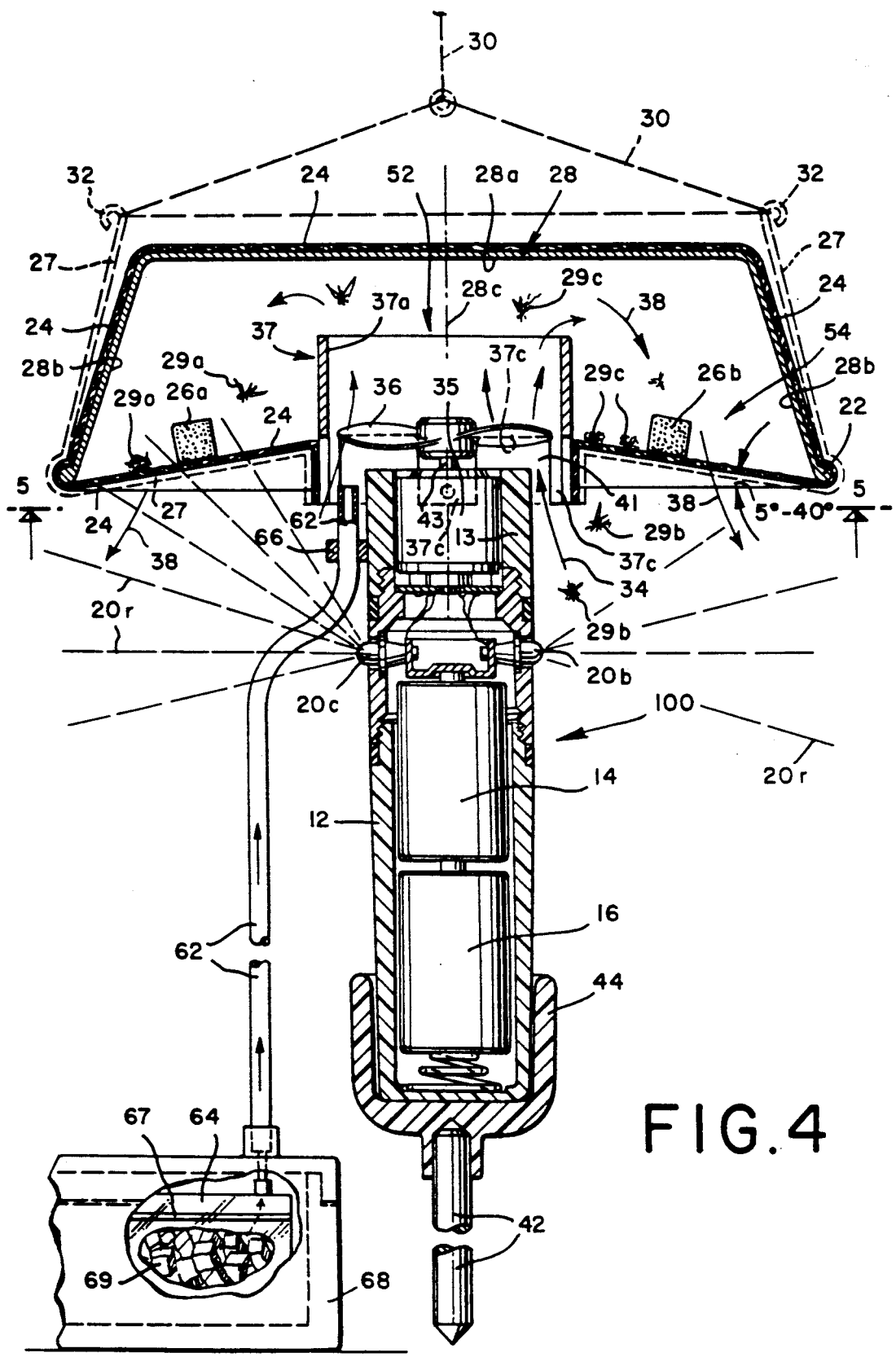
FIG. 4 is a cut-away side elevation view of the semiochemical field trap for blood feeding arthropods of FIG. 1 showing blood feeding arthropods inside the trap being attracted to semiochemical-containing matrices comprising a porous containment agent containing in the interstices thereof at least one semiochemical sustainably releaseable therefrom.
Figure 5:
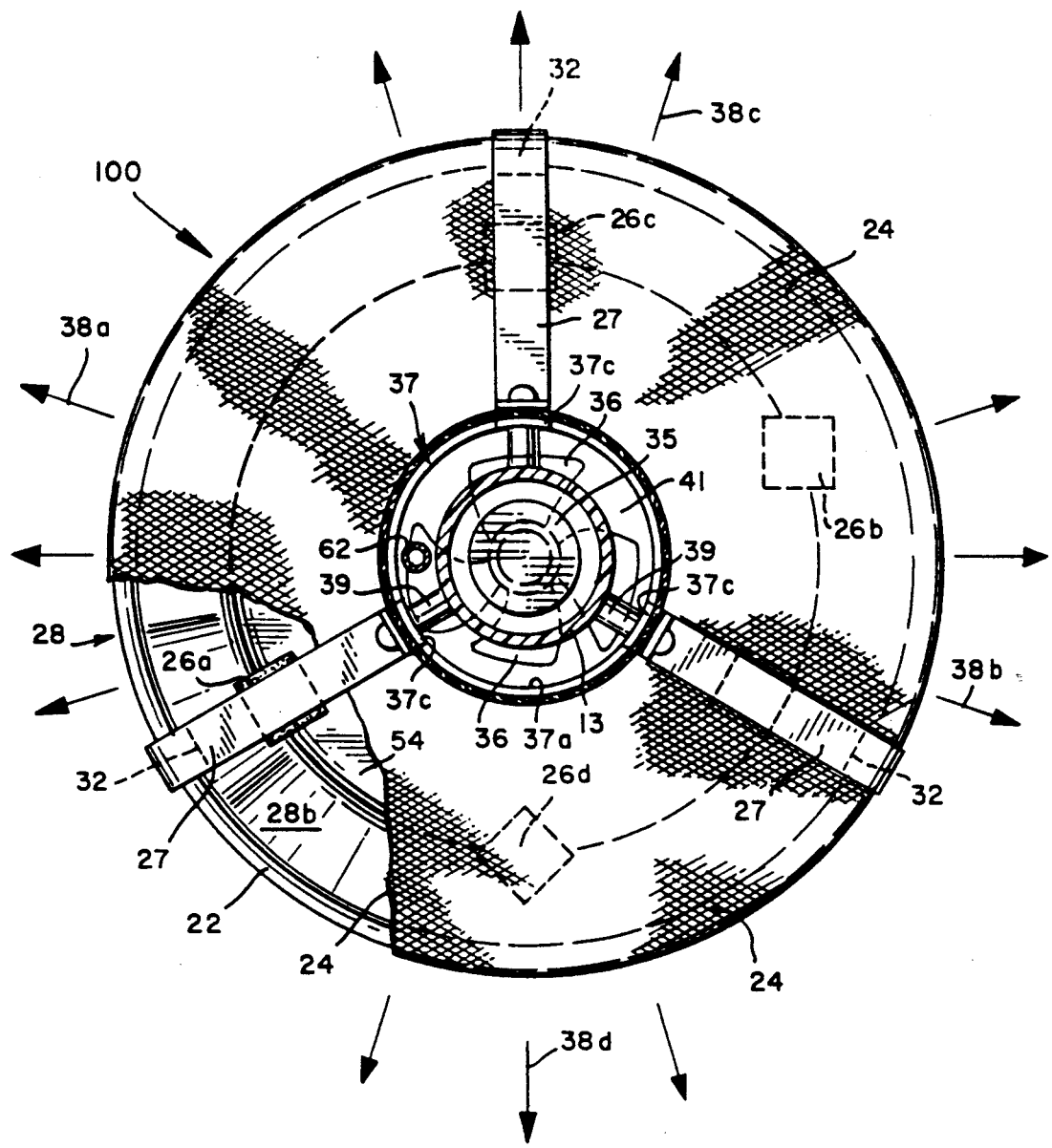
FIG. 5 is a bottom view of the semiochemical field trap for blood feeding arthropods of FIG. 4 looking in the direction of the arrows along line 5—5.

Referring to FIGS. 1-6, a semiochemical field trap 100 for blood feeding arthropods 29 comprises:

(1) An upright vertically-disposed first hollow outer housing 28 having substantially rigid arthropod-impermeable first side walls 28b, an upper arthropod-horizontal surface 28a substantially entirely contiguous with said first side walls 28b and a substantially entirely open bottom 28d having a substantially horizontal plane substantially perpendicular to the vertical axis 28c of said first hollow outer housing 28;

(2) Located along an axis 28c substantially perpendicular to the horizontal plane 28d of said substantially entirely open bottom of said first outer housing 28, substantially parallel to the vertical axis 28c of said first hollow housing 28, and within said first hollow housing 28, a second inner hollow housing 37, having a hollow interior, opposite open upper first and lower second ends, vertically-disposed rigid arthropod-impenetrable side walls 37a, and a longitudinal dimension extending between the two ends, said upper first end being at a substantial distance below said upper substantially horizontal surface 28a of said first outer housing 28;

(3) Extending outwardly from said substantially vertically disposed side walls 37a of said second inner hollow housing 37 to the side walls 28b of the first hollow outer housing 28, at an angle of from about −5° up to about −40°, measured downwardly from the substantially horizontal plane 28d of the open bottom of said first hollow outer housing 28, substantially rigid rib components 27, which enabled the fixed positioning of said inner hollow housing 37 with respect to the positioning of and within said outer hollow housing 28;

(4) Completely encompassingly traversing in a substantially tight fitting manner the area between (i) the first side walls 28b of said first outer hollow housing 28, and (ii) the second side walls 38a of said second inner hollow housing 37 along the directional vectors of said rib components 27 and in a curvilinear plane below and substantially contiguous to said rib components 27, a continuous substantially macroporous mesh substance 24, having such a mesh size as to be impenetrable by arthropods 29 sought to be entrapped, but pervious to gas and liquid and, in addition, radiation transmittable, and capable of supporting a matrix article, as indicated by reference numerals 26, 26a, and 26b containing sustainably releasable semiochemical;

(5) At least one semiochemical-containing matrix 26, 26a, and 26b comprising a porous containment agent containing in the interstices thereof at least one semiochemical sustainably releasable therefrom, located on the upper surface of said macroporous mesh substance, 24;

(6) A sustainably vertically disposed drive shaft 43 supported for rotary motion about its axis 28c, extending from below and into the hollow interior of said inner hollow housing 37 along the said longitudinal dimension thereof;

(7) Motor means 35 connected to a first lower end of said drive shaft 43 for rotating said drive shaft 43 about its axis 28c;

(8) Air flow creation means 36 attached to the second upper end of said drive shaft 43, being of such a design whereby the rotation of said drive shaft 43 directly causes the rotation of said air flow creation means 36 and induces the flow of air 34 from beneath said second inner hollow housing upwardly into the 3-space 52, 54 within said first hollow outer housing 28 between the outer side wall of the second inner hollow housing 37 and the inner side wall 28b of said first outer hollow housing 28;

(9) Radiation emission means 20 for emission of radiation 20r of a specific wave length or of a range of wave lengths outwardly from the apparatus 100 located in the vicinity of the lower portion of said second inner hollow housing 37, below the location of said rib components 27;

(10) At least one power supply means 14, 16 associated with said trap 100 energizing said radiation means 20 and said motor means 35 on engagement of the power supply means 14, 16 with said motor means 35 and said radiation emission means 20;

whereby arthropods 29b in the vicinity of said trap 100 are attracted by said radiation 20r to a location so close to said trap 100 that in the event that an attracting chemical in said matrix 26, 26a, 26b is detected by said arthropods 29b, said arthropods will enter the air stream 34 created by said air flow creation means 36, and be carried through location 41 into the 3-space 52, 54 within said first hollow outer housing 28 between the outer side wall 37a of said inner hollow housing 37 and the inner side wall 28b of said first outer hollow housing 28.

In the preferred embodiment shown in the drawings, there is shown a semiochemical field trap 100 for blood feeding arthropods 29 comprising:

(1) An upright hollow frustum of a cone or polyhedron 28 having three or more gas and liquid-impervious sides 28b, a gas and liquid-impervious top surface 28a having surface area $A_1$ and radius $R_1$ and a substantially entirely open bottom 28d circumscribed by an outer rim 22, said bottom 28d having area $A_2$ and radius $R_2$ with $A_1 < A_2$ and $R_1 < R_2$; the plane of said top surface 28a being substantially parallel to the plane of said substantially entirely open bottom 28d, the distance from said top surface 28a to said bottom plane at 28d being $D_1$;

(2) Located along an axis 28c substantially perpendicular to said top surface 28a of said upright hollow frustum 28, and said open bottom plane 28d of said frustum 28 a hollow vertically-disposed open-ended cylinder 37 having height $D_3$ and radius $R_3$, having open first and second ends, a gas and liquid-impervious side wall 37a and a vertical longitudinal dimension extending between the two ends, said cylinder 37 being substantially coaxial with said upright hollow frustum 28, a substantial portion, f, of said cylinder 37 being located between said upper surface 28a of said frustum 28 and said lower plane 28d of said frustum with $f \leq 1$, said upper end of said cylinder 37 being beneath and a finite distance $D_4$ from the upper surface of said frustum 28a, with $R_3 < R_1$, $R_3 < R_2$ and $D_4 < D_1$;

(3) Extending outwardly from the side wall 37a of said cylinder 37 at an angle of from $-5°$ down to $-40°$, subtended downwardly from the plane 28d of the open bottom of said frustum with the vertex of the angle at said outer wall of said cylinder, substantially rigid rib components 27 fixedly connecting the lower rim 22 of said frustum 28 to said side wall of said cylinder 37a whereby said cylinder 37 is fixedly positioned with reference to said frustum 28 and is fixedly coaxial with said frustum 28;

(4) Substantially completely encompassingly traversing in a tight fitting manner, the area between the vertical side wall 37a of said cylinder 37 and said outer rim 22 of said frustum along the directional vectors of, in a curvilinear plane below, and contiguous to said rib components 27, a continuous substantially monolaminar macroporous mesh substance 24 having such a mesh size as to be impenetrable by arthropods 29 sought to be entrapped but pervious to gas and liquid and being radiation 20r transmittable, and being capable of supporting at least one substantially solid matrix article 26 containing one or more substantially sustainably releasable semiochemical substance;

(5) At least one substantially solid semiochemical-containing matrix 26, 26a and 26b located on said monolaminar macroporous mesh substance 24 comprising a porous solid containing in the interstices there of a semiochemical sustainably releasable from the solid matrix 26, 26a and 26b in a sustained release manner;

(6) A substantially vertically disposed drive shaft 43 having a first lower end and a second upper end, said drive shaft 43 being coaxial with said open-ended cylinder 37 and being supported for rotary motion about its axis 28a, said drive shaft 43 extending from below and into the hollow interior of said cylinder 43;

(7) Motor means 35 connected to said lower end of said drive shaft 43 for rotating said drive shaft 43;

(8) A propeller 36 attached to said second upper end of said drive shaft 43 said propeller 36 being rotatable in a plane substantially parallel to the plane 28d of said open bottom of said frustum 28 and substantially perpendicular to the axis 28a of said drive shaft 43, said propeller 36 having an effective radius, $R_4$, with $R_4 < R_3$, whereby the rotation of said drive shaft 43 rotates said propeller 36 and induces a flow of air 34, 38 from beneath said cylinder 36, upwardly into the 3-space 52, 54, within said frustum 28 between the side wall 37a of the cylinder 37 and the side wall of said frustum 28b;

(9) Radiation emission means 20, 20a, 20b and 20c (shown in detail in FIG. 6) for emission of radiation 20r of a wave length or a range of wave lengths outwardly from the trap 100 said radiation means 20 being located in the proximity of the lower portion of said cylinder 37 below the location of said substantially rigid rib components 27, the geometric configuration and location of said radiation means 20 being such that at least a portion of the radiation 20r generated by said radiation emission means reaches the curvilinear plane traversed by said macroporous mesh substance 24;

(10) At least one electric power supply 14, 16 (e.g., direct current batteries) associated with said trap 100 causing said radiation emission means 20 to generate radiation 20r into energizing said motor means;

whereby arthropods 29 in the vicinity of said trap 100 are attracted by radiation 20r generated by said radiation emission means 20 to a location so close to said trap that in the event an attractant in said matrix 26, 26a, 26b and 26c is detected by said arthropods 29, said arthropods 29 will enter the upwardly moving air stream 34 and be carried into the 3-space 52, 54 within said frustum 28 between the wall of the cylinder 37a and the side wall of said frustum 28b.

Switch (shown in the form of a push "on", release "off" switch) 18 is located at a point midway between the location of the lower most portion of the cylinder 36 and the lower most portion of the power supply 14, 16. Power supply (shown as direct current batteries) 14, 16 is encased and vertically juxtaposed in hollow cylinder 12. The entire trap 100 is held in an upright position, for example, in cup 44 mounted on stand 42 which is placed into the ground when in use. As soon as the trap 100 is placed into the ground, switch 18 is placed in an "on" position thereby causing electric power supply 14, 16 to energize motor means 35 which in turn rotates drive shaft 43 causing propeller 36 to rotate causing air to be sucked into the 3-space, 52, 54 within frustum 28. The air flows out as shown by arrows 38 through the mesh 24 past the matrix 26 which holds semiochemicals such as KOAVON®, KOAVOL DH® or LYRAME®. In the event that the material in matrix 26 is a repellent for a given species of insects, e.g., *Musca domestica* L. (Diptera Muscidae), then virtually no *Musca domestica* L. (Diptera Muscidae) will enter air stream 34 to be trapped within the 3-space 52, 54. On the other hand, if an attractant is contained in matrix 26 which is an attractant for example, *Musca domestica* L. (Diptera Muscidae), then the *Musca domestica* L. (Diptera Muscidae) will enter the air stream 34 and be trapped in 3-space 52, 54 and remain there as a result of its attractancy to radiation 20r emitted from radiation means 20, as well as carbon dioxide flowing through tube 62.

Referring to the carbon dioxide flow, dry ice particles 69 or "chunks" is placed into zipper-locked bag 64 with zip-lock 67. The bag is connected to tube 62, and tube 62 is mounted at mount 66 beneath cylinder 37 but in the space 41 between cylinder 37 and the cylinder 100 which holds the power supply means 14, 16, and motor means 35. The zip-locked bag 64 is contained in insulated container 68. As soon as the switch 18 is turned on in order to engage power supply means 14, 16 with motor means 35, a pinch clamp is removed from tube 62 enabling carbon dioxide to flow through tube 62 into the 3-space surrounding propeller 36 at location 41. The carbon dioxide alone acts as an attractant for the species of insects:

(a) *Musca domestica* L. (Diptera Muscidae);
(b) *Aedes aegypti;*
(c) *Aedes albopictus;*
(d) Anopheles spp.;
(e) *Coquillettidia perturbans;*
(f) Culiseta spp.;
(g) Culex spp.;

(h) Psorophora spp.;
(i) Culicoides spp.; and/or
(j) Lutzomyia spp.

If desired, the trap 100 may also or in the alternative to being placed in the ground through stake 12, be suspended from suspension 30 held by clips 32.

Referring to FIG. 6, FIG. 6 is a schematic diagram of the circuit which includes the radiation emission means 20a, 20b and 20c. Radiation emission means 20a, 20b and 20c are lightbulbs such as green light emitting diodes or infrared light emitting diodes, as explained in detail supra. Resister 56 may be a resister of from about 10 up to about 30 ohms. Button switch 18 is shown in the circuit as such and electric power supply means is shown diagramatically using the same reference numerals 14 and 16.

Figure 25:
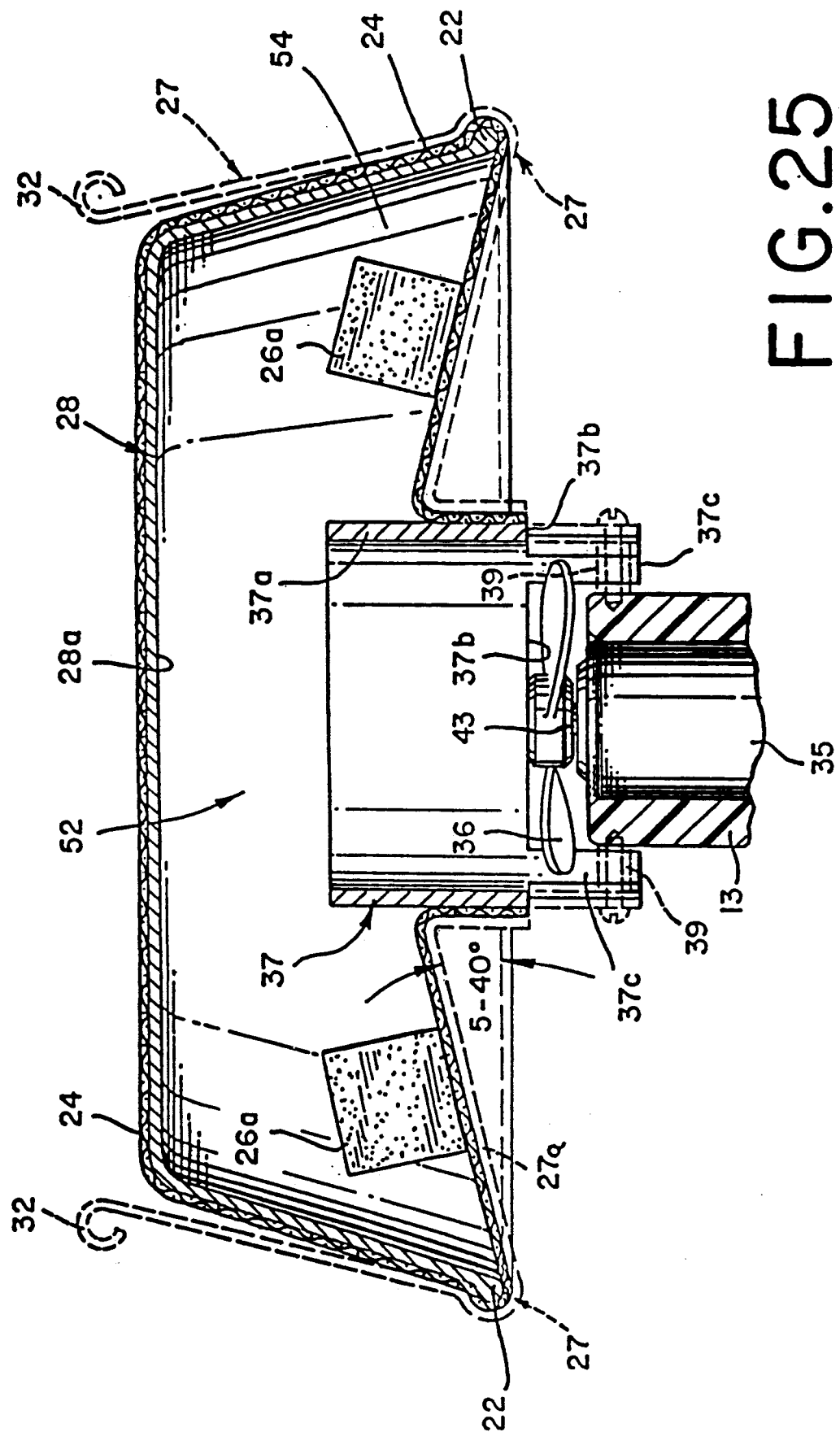
FIG. 25 is a cut-away side elevation view of a detailed section of the semiochemical field trap for blood feeding arthropods of our invention showing in detail the air flow creation means attached to the drive shaft and its relationship with the semiochemical containing matrix comprising a porous containment agent containing in the interstices thereof at least one semiochemical sustainably releasable therefrom located on the upper surface of the macroporous mesh substance, e.g. the nylon mesh.

FIG. 25 is a detailed cut-away side elevation view of a preferred embodiment of the trap of our invention. In this embodiment, as shown in FIG. 25, the propeller 36 is located in a plane at the bottom level of cylinder 37 shown by reference numeral 37b. Of course, cylinder 37 must be fixedly positioned and is thus positioned in relation to cylinder 12 by using screw mounts 39 with extensions of cylinder 37 only where the screw mounts are located, the extensions being shown by reference numeral 37c.

FIGS. 7, 8, 9 and 10 set forth bar graphs (number of insects versus treatment) of data for insects attracted or repelled using the apparatus of FIGS. 1-6 and 25.

Figure 7:
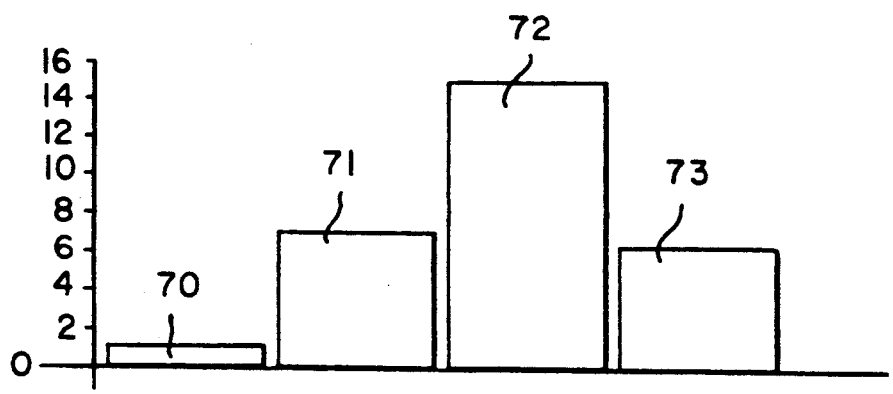
FIG. 7 is a bar graph showing a comparison of field trial tests of attractants for gnats, (that is, Culicoides spp. and Lutzomyia spp.) comparing the use of the semiochemical field trap for blood feeding arthropods of our invention using no light emitting diode, using only carbon dioxide with the use of a light emitting diode, using a mixture of alpha-terpineol and dibutyl succinate and then using a mixture of benzaldehyde and butyl acetate, the graph being treatment versus mean number of gnats trapped in the semiochemical field trap for blood feeding arthropods of our invention. The data for the graph of FIG. 7 is set forth in Table III, infra.

FIG. 7, is a bar graph showing mean number of gnats per treatment (trapped in trap 100) versus treatment. The bar graph indicated by reference numeral 70 is one where carbon dioxide is supplied through tube 62, but the light emitting diodes 20a, 20b and 20c are not engaged. Bar graph 71 is indicative of the mean number of insects trapped when using carbon dioxide being supplied through tube 62 and with the light emitting diode "green light" being engaged.

The insects which are the subject of FIG. 7 are the gnats to wit: Culicoides spp. and Lutzomyia spp.

The bar graph indicated by reference numeral 72 shows the mean number of gnats trapped as a result of utilizing a mixture of alpha terpineol and dibutyl succinate in matrix 26.

The bar graph indicated by reference numeral 72 is the bar graph showing mean number of gnats trapped as a result of using a mixture of benzaldehyde and butyl acetate.

The following Table III is a numerical table summarizing the graph of FIG. 7:

TABLE III

| Treatment | Replicate 1 | Replicate 2 | Replicate 3 | Replicate 4 | Mean |
|---|---|---|---|---|---|
| GREEN LED TRAP WITH CARBON DIOXIDE GNATS PER REPLICATION | | | | | |
| Carbon dioxide but no light emitting diode used | 0 | 2 | 0 | 2 | 1.00 |
| Use of carbon dioxide together with engagement of green light emitting diode | 6 | 4 | 6 | 12 | 7.00 |
| Use of carbon dioxide supplied through tube 62, engagement of light emitting diode 20a, 20b and 20c (green light) and use of mixture of alpha terpineol and dibutyl succinate in matric 26 | 8 | 7 | 26 | 19 | 15.00 |
| Use of carbon dioxide supplied through tube 62, engagement of green light emitting diode and presence of mixture of benzaldehyde and butyl acetate in matrix 26 | 6 | 8 | 6 | 5 | 6.25 |

Figure 8:
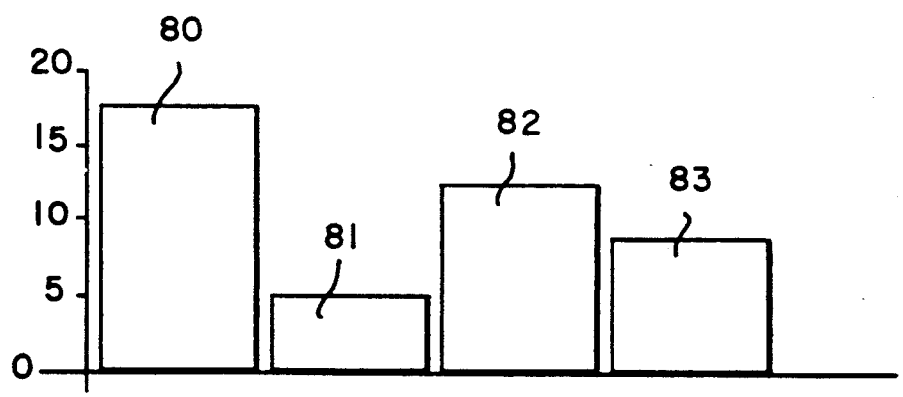
FIG. 8 is a bar graph showing a comparison of the field trial tests of attractants for gnats (that is, Culicoides spp. and Lutzomyia spp.), comparing the system without the use of any light emitting diode, the system using only carbon dioxide with a green light emitting diode, cinnamic acid, and 0.0001% marigold absolute, the graph being treatment versus mean number of gnats. The data for the graph is set forth in Table IV, infra.

FIG. 8 is a group of bar graphs showing mean number of gnats per treatment versus particular treatment, the gnats being: Culicoides spp. and Lutzomyia spp. The bar graph indicated by reference numeral 80 shows only the use on engagement of the light emitting diodes 20a, 20b and 20c without supplying carbon dioxide through tube 62. The bar graph indicated by reference numeral 81 shows the use of green light emitting diode engaged as a result of turning switch 18 "on". The use of the light emitting diode is in conjunction with the supplying of carbon dioxide through tube 62.

The bar graph indicated by reference numeral 82 is the bar graph for the use of the green light emitting diode taken together with supplying of $CO_2$ through tube 62 and the use of cinammic acid in matrix 26. The bar graph indicated by reference numeral 83 shows the mean number of gnats attracted into the trap as a result of using $CO_2$ supplied through tube 62; a green light emitting diode engaged as a result of turning switch 18 to a "on" position and the use of a 0.001% concentration of marigold absolute contained in a polyethylene-vinyl acetate matrix 26 on mesh 24.

Table IV summarizes the data shown in in the bar graph of FIG. 8.

TABLE IV

| Treatment | Replicate 1 | Replicate 2 | Replicate 3 | Replicate 4 | Mean |
|---|---|---|---|---|---|
| SEMIOCHEMICAL FIELD TRAP TRIAL WITH GREEN LIGHT EMITTING DIODE TRAP | | | | | |
| Use of green light emitting diode but no carbon dioxide supplied | 19 | 14 | 10 | 28 | 17.75 |
| Use of light emitting diode (green) simultaneously with supplying of carbon dioxide through tube 62 | 3 | 0 | 14 | 3 | 5.00 |
| Use of cinammic acid, an attractant in matrix 26 together with engagement of green light emitting diode and supplying of $CO_2$ through tube 26 | 26 | 10 | 7 | 7 | 12.50 |
| Use of light emitting diode (green) together with | 0 | 5 | 3 | 27 | 8.75 |

TABLE IV-continued

SEMIOCHEMICAL FIELD TRAP TRIAL WITH GREEN LIGHT EMITTING DIODE TRAP

| Treatment | Replicate 1 | Replicate 2 | Replicate 3 | Replicate 4 | Mean |
|---|---|---|---|---|---|
| supplying of $CO_2$ through tube 62 and containment of 0.001% marigold absolute in ethylene-vinyl acetate polymer matrix 26 | | | | | |

Figure 9:
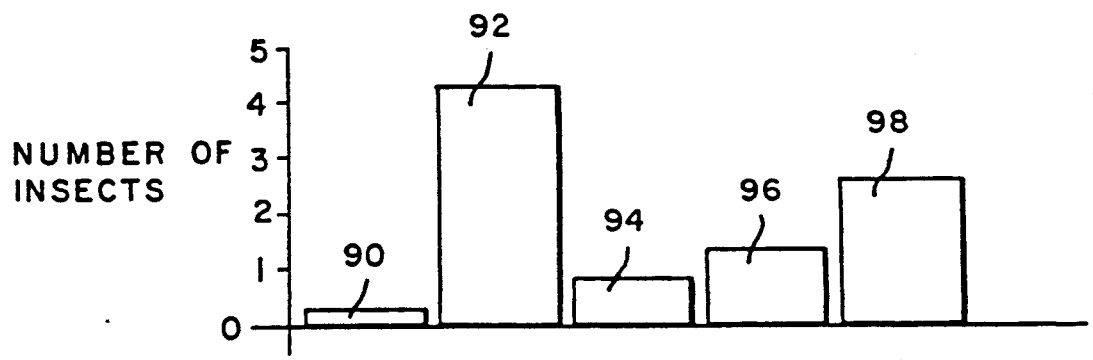
FIG. 9 is a bar graph showing a comparison of the field trial tests in the semiochemical field trap for blood feeding arthropods of our invention of repellents against mosquitoes, e.g., *Aedes aegypti, Aedes albopictus*, Anopheles spp., *Coquillettidia perturbans*, Culiseta spp., Culex spp., and Psorophora spp., comparing the use of infrared light emitting diodes alone, the combination of infrared light emitting diodes with carbon dioxide, KOAVONE®, KOAVOL DH®, and LYRAME® Each of the KOAVONE®, KOAVOL DH® and LYRAME® being used with the infrared light emitting diode and carbon dioxide, the graph being treatment versus insects per treatment trapped in the semiochemical field trap for blood feeding arthropods of our invention. The data supporting the graph of FIG. 9 is set forth in Table V, infra.

FIG. 9 is a bar graph showing mean number of mosquitoes per treatment versus treatment with the mosquitoes being trapped in trap 100 being:

(a) *Aedes aegypti;*
(b) *Aedes albopictus;*
(c) Anopheles spp.;
(d) *Coquillettidia perturbans;*
(e) Culiseta spp.;
(f) Culex spp.;
(g) Psorophora spp.

The bar graph indicated by reference numeral 90 is a bar graph using an infrared light emitting diode but no carbon dioxide being supplied through tube 62. The infrared light emitting diode is indicated again by reference numerals 20a, 20b and 20c. The bar graph indicated by reference numeral 92 is for the use of an infrared light emitting diode together with supplying of $CO_2$ through tube 62.

The bar graph indicated by reference numeral 94 is the bar graph when engaging the light emitting diode for infrared light and using a carbon dioxide supply through tube 62 and in addition admixing KOAVONE ® with the microporous polymer of ethylene and vinyl acetate indicated by reference numeral 26.

The graph indicated by reference numeral 96 is the graph showing mean number of mosquitoes trapped in trap 100 when KOAVOL DH ® is in the microporous polymer block 26, and also using the infrared light emitting diode and a $CO_2$ supplied through tube 62.

The graph indicated by reference numeral 98 is the graph of mean number of mosquitoes trapped when using an infrared light emitting diode 20, carbon dioxide supplied through tube 62 and LYRAME ® in matrix 26. The data on which the graph of FIG. 9 is based is set forth in the following Table V.

TABLE V

SEMIOCHEMICAL FIELD TRAP TRIAL USING INFRARED LIGHT EMITTING DIODE AND CARBON DIOXIDE SUPPLY (MOSQUITOES PER REPLICATION)

| Treatment | Replicate 1 | Replicate 2 | Replicate 3 | Replicate 4 | Mean |
|---|---|---|---|---|---|
| Use of infrared light emitting diode but no carbon dioxide being supplied through tube 62 | 0 | 0 | 0 | 1 | 0.25 |
| Use of infrared light emitting diode with carbon dioxide being supplied through tube 62 | 1 | 0 | 6 | 10 | 4.25 |
| Use of infrared light emitting diode with carbon dioxide supplied through tube 62 and KOAVONE ® contained in matrix 26 | 1 | 1 | 0 | 1 | 0.75 |
| Use of infrared light emitting diode with carbon dioxide supplied through tube 62 and KOAVOL DH ® contained in matrix 26 | 1 | 0 | 2 | 2 | 1.25 |
| Use of infrared light emitting diode with carbon dioxide supplied through tube 62 and LYRAME ® contained in matrix 26 | 3 | 3 | 3 | 1 | 2.80 |

Figure 10:
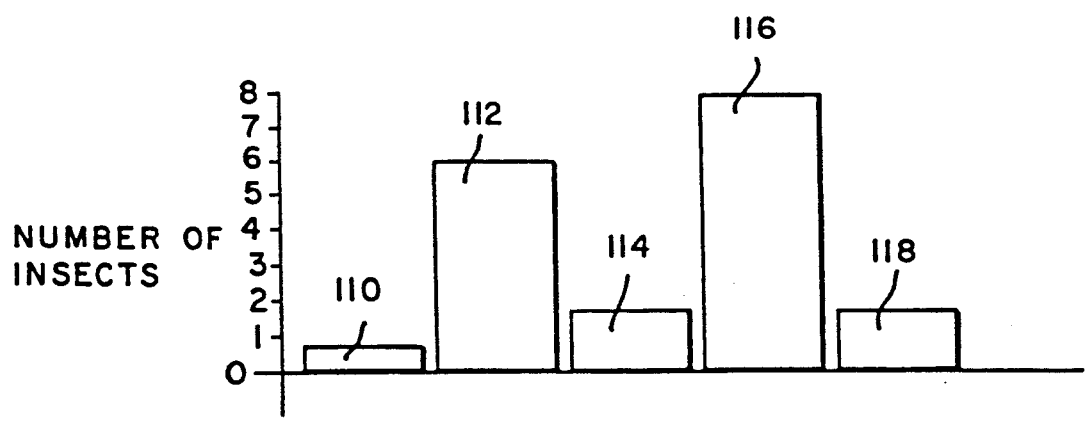
FIG. 10 is a bar graph showing a comparison of the field trial tests of repellents for the gnats, Culicoides spp. and Lutzomyia spp., comparing the use of infrared light (using an infrared light emitting diode) with no $CO_2$, the use of infrared light with the use of $CO_2$, the use of KOAVONE®, or KOAVOL DH® or LYRAME® with infrared light and $CO_2$, the graph being treatment versus mean number of insects per treatment. The data supporting the graph of FIG. 10 is set forth in Table VI, infra.

FIG. 10 is a bar graph of mean number of gnats trapped versus treatment using trap 100 with the gnats being: Culicoides spp. and Lutzomyia spp. The bar graph indicated by reference numeral 100 is the graph for the mean numer of gnats trapped using an infrared light emitting diode but no carbon dioxide being supplied through tube 62. The bar graph indicated by reference numeral 112 is the bar graph for the mean number of gnats trapped when using an infrared light emitting diode and supplying carbon dioxide through tube 62.

The bar graph indicated by reference numeral 114 is the bar graph for mean number of gnats trapped when using an infrared light emitting diode 20, carbon dioxide supplied through tube 62 and KOAVONE ® contained in matrix 26. The bar graph indicated by reference numeral 116 is the bar graph for the mean number of gnats trapped in trap 100 when using an infrared light emitting diode, carbon dioxide supplied through tube 62 and KOAVOL DH ® contained in matrix 26. The graph indicated by reference numeral 118 is the graph for mean number of gnats trapped when using an infrared light emitting diode, carbon dioxide supplied through tubes 62 and LYRAME ® contained in matrix 26.

Table VI sets forth the data on which the graph shown in FIG. 10 is based.

TABLE VI

SEMIOCHEMICAL FIELD TRAP TRIAL; INFRARED LIGHT EMITTING DIODE TRAP WITH $CO_2$ SUPPLY; GNATS PER REPLICATION

| Treatment | Replicate 1 | Replicate 2 | Replicate 3 | Replicate 4 | Mean |
|---|---|---|---|---|---|
| Use of infrared light emitting diode without supplying carbon dioxide through tube 62 | 0 | 0 | 2 | 1 | 0.75 |
| Use of infrared light emitting diode with supply of carbon dioxide through tube 62 | 1 | 6 | 1 | 16 | 6.00 |
| Use of infrared light emitting diode with supply of carbon dioxide through tube 62 and KOAVONE ® | 1 | 5 | 1 | 0 | 1.75 |

TABLE VI-continued

SEMIOCHEMICAL FIELD TRAP TRIAL; INFRARED LIGHT EMITTING DIODE TRAP WITH $CO_2$ SUPPLY; GNATS PER REPLICATION

| Treatment | Replicate 1 | Replicate 2 | Replicate 3 | Replicate 4 | Mean |
|---|---|---|---|---|---|
| in matrix 26 | | | | | |
| Use of infrared light emitting diode with supply of carbon dioxide through tube 62 and KOAVOL DH ® in matrix 26 | 10 | 3 | 3 | 16 | 8.00 |
| Use of infrared light emitting diode with supply of carbon dioxide through tube 62 and LYRAME ® in matrix 26 | 1 | 1 | 1 | 4 | 1.75 |

Figure 11:
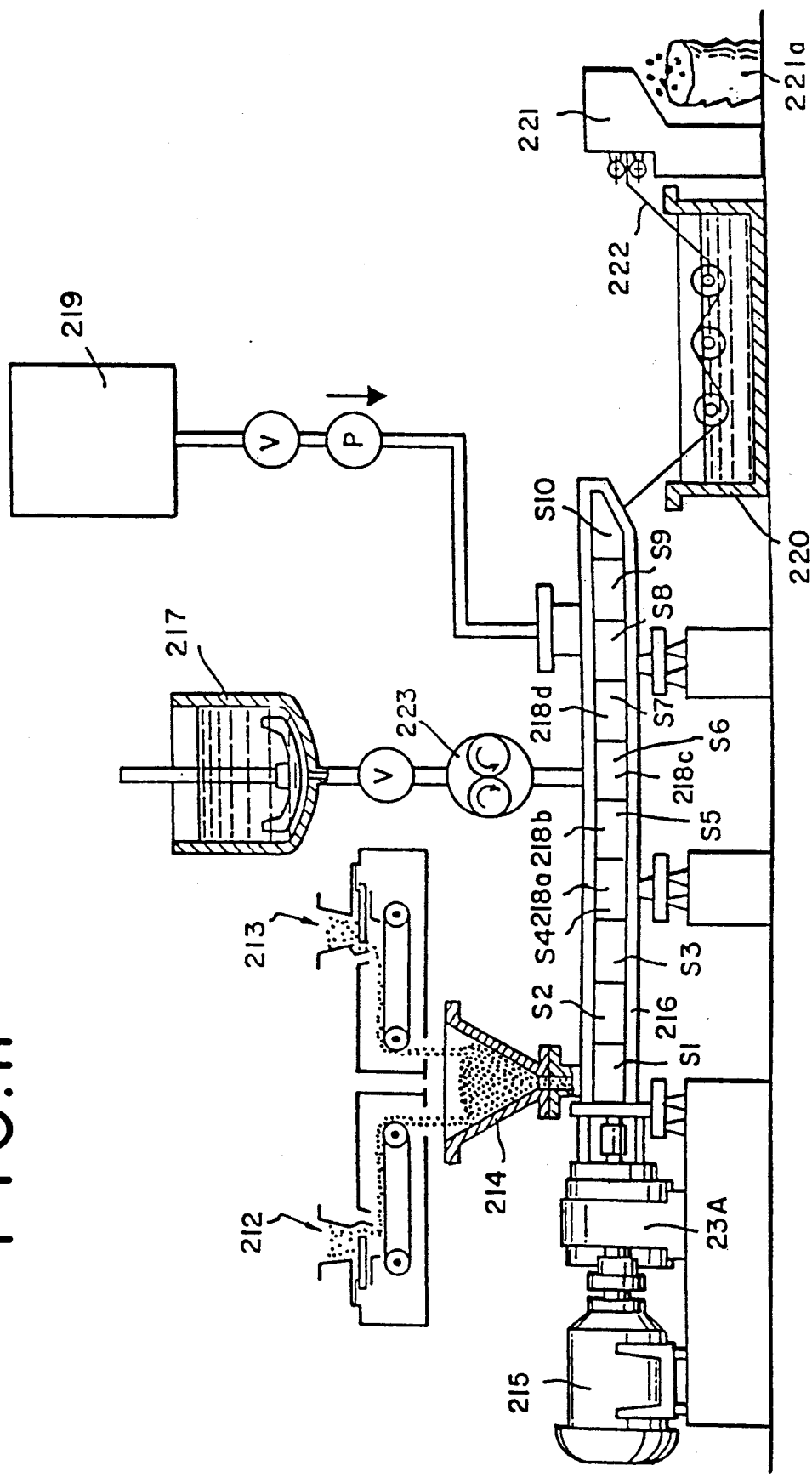
FIG. 11 is a cut-away side elevation schematic diagram of a screw extruder during the compounding of a resin with insect repellents, including one or more of the ketone, alcohol or schiff base of our invention while simultaneously adding foaming agent into the hollow portion of the barrel of the extruder and incorporates the pelletizing apparatus used in the of the extruded foamed tow product produced as a result of the extrusion operation.

Regarding FIG. 11, FIG. 11 is a schematic cut-away elevation diagram of an extrusion and pelletizing apparatus useful for the fabrication of matrix 26 used in carrying out a process of our invention. The operation of the apparatus causes an insect attractant or repellent to be incorporated into a polymer such as a polyethylene. Motor 215 drives the extruder screws located at 223a in barrel 216a, the extruder being operated at temperatures in the range of from about 150° C. up to about 250° C. At the beginning of the barrel, resin at source 212 together with additives, e.g., processing aides and densifiers at location 213 is added via addition funnel 214 into the extruder. Simultaneously (when the operation reaches "steady state"), insect repellent, e.g., the KOAVONE ® of our invention is added to the extruder at one or more barrel segments, S-3, S-4, S-5, S-6, S-7 and S-8 of the extruder (which may be a twin screw or single screw extruder) at locations 218a, 218b, 218c and 218d (for example) by means of gear pump 223 from source 217. From source 219 into barrel segments S-5, S-6, S-7, S-8, S-9 and S-10, a gaseous or liquid blowing agent, e.g., nitrogen, carbon dioxide and the like are added simultaneously with the addition of insect repellent, e.g., the KOAVONE ® of our invention. The feed rate range of resin is about 80-300 pounds per hour. The feed rate range of insect attractant or repellent is between 1 and 35% of the feed rate range of the resin. The blowing agent range is such that the pressure of the gas or the pressure over the liquid being fed into the extruder is between about 50 and 200 psig if, indeed, blowing agent is added. If desired the extruded ribbon or cylinder may be passed through water bath 220 and pelletizer 221 into collection apparatus 221a.

A preferred embodiment of our invention set forth in FIGS. 12-21 comprises an ellipsoidally-shaped detergent tablet 830 containing a solid plastic core 832 which can be fabricated from, for example, polyethylene, polypropylene, nylon or any polymer capable of having therein microvoids from which an insect repelling substance, e.g., KOAVONE ® will be controllably transported from the plastic core into and through the soap cake over a reasonable period of time during the use of the soap cake. Such polymers can be microporous polymers such as those described in U.S. Pat. No. 4,247,498 issued on Jan. 27, 1981, the specification for which is incorporated herein by reference. Surrounding the central plastic core containing insect repellent 832 is detergent 830' which is in the solid phase at ambient conditions, e.g., room temperature and atmospheric pressure. Examples of workable detergents 830' are "elastic" detergents such as those described in U.S. Pat. No. 4,181,632 issued on Jan. 1, 1980, the disclosure of which is incorporated herein by reference, or "transparent" soaps such as those set forth in U.S. Pat. No. 4,165,293 issued on Aug. 21, 1979, the disclosure of which is incorporated herein by reference. Other examples of the detergent 830' useful in our invention are those set forth as "variegated soaps" in Canadian Letters Patent No. 1,101,165 issued on May 19, 1981, the disclosure of which is incorporated by reference herein.

On use of the soap table 830 or detergent bar, the insect repellent agent, e.g. KOAVONE ®, KOAVOL DH ® and/or LYRAME ®, originally located in plastic core 832 is transported at a steady state from core 832 through core surface 831 through the detergent 830' and finally through the surface of the detergent bar at, for example, 833, 834, 835 and 836.

The detergent bar or tablet 830 of our invention may be of any geometric shape, for example, a rectangular parallelpiped tablet as shown in FIGS. 16, 17 and 18 containing solid plastic core 839. The insect repellent located in solid plastic core 839 on use of the detergent bar passes through at steady state, surface 832 of FIG. 17, detergent 838 and finally surface 839 at, for example, locations 840, 841, 842 and 843. The environment surrounding the detergent bar on use thereof is then treat insect repellent, e.g., KOAVOL DH ®, at 843, 844 and 845. Optionally, aromatizing agent can also be contained in the detergent bar and so the environment surrounding the detergent bar on use thereof would also be aesthetically aromatized at 843, 844 and 845, for example.

As shown in FIGS. 19, 20 and 21 the plastic core of the detergent tablet 830 may have a single finite void at its center 851 (of FIGS. 20 and 21) in which the insect repellent agent and optionally the aromatizing agent is contained. The plastic core then is a shell 848 having outer surface 852 (shown in FIGS. 20 and 21). The insect repellent agent (and optionally the aromatizing agent) contained in the void in the plastic core permeates through shell 848, past surface 852 at a steady state, through the detergent 847 and to the environment at, for example, 856, 857, 858 and 859.

In addition to the insect repellent contained in the core, e.g., core 839 or core void the core can also contain other materials for therapeutic use, for example, bacteriostats, deodorizing agents and the like which are compatible with insect repellents such as the ketone, alcohol and schiff base of our invention. In the alternative, the plastic core of the detergent tablet of FIGS. 19, 20 and 21 may have an empty single finite void at its center 851 with the insect repellent contained in the shell 848.

At the end of the use of the detergent tablet, the hollow core or the solid core can be used as an insect repelling and aroma imparting or air freshener household article. In addition, depending on the ratio of the volume of the void 851, to the solid part of the detergent tablet of FIGS. 19, 20 and 21, the detergent tablet of FIGS. 19, 20 and 21 can be so fabricated that it will float on the surface of the liquid in which it is being used and this physical attribute has certain obvious advantages.

Figure 24:
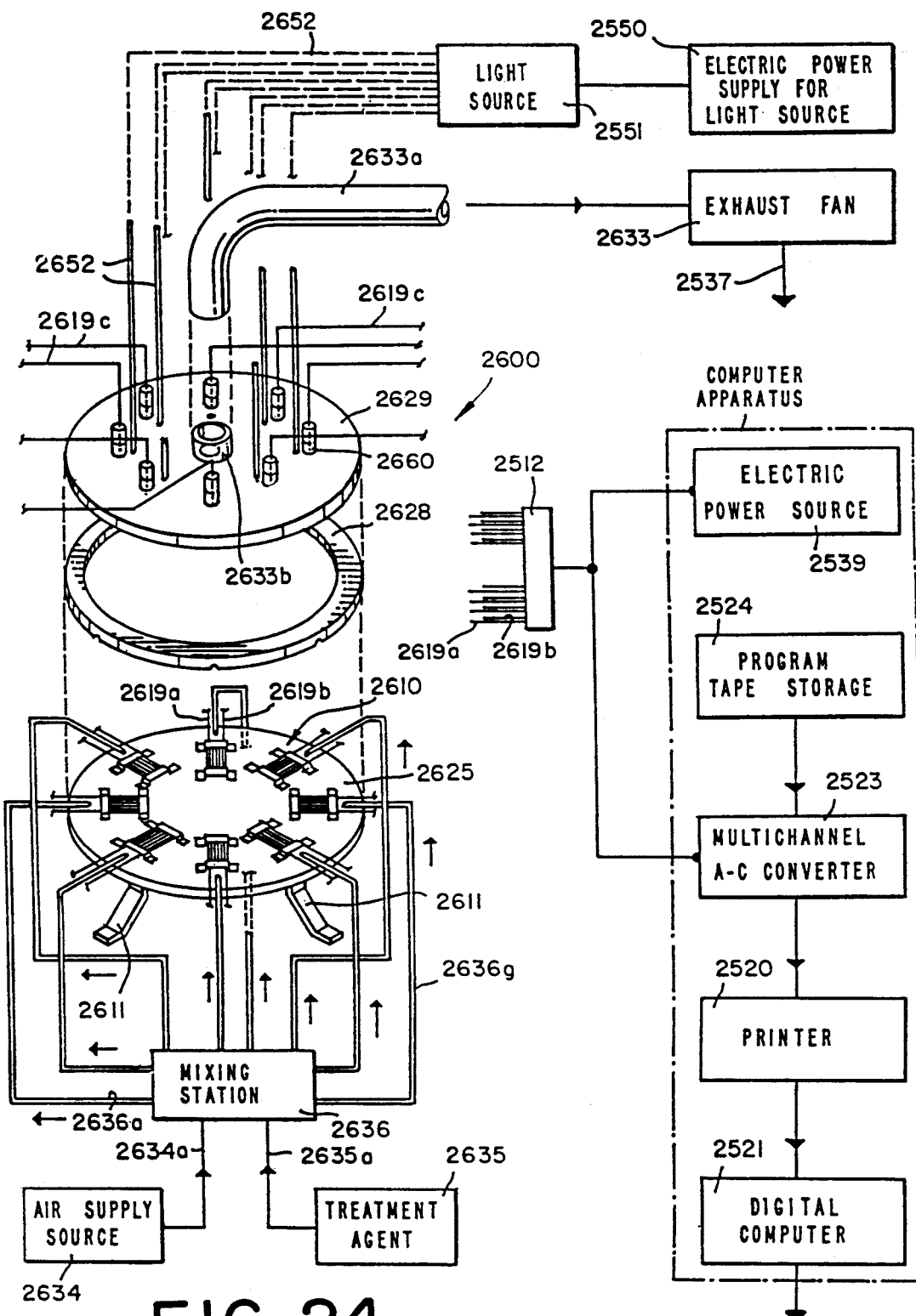
FIG. 24 is a schematic diagram (blown up for illustration purposes) of a prior art olfactometer apparatus (of application for U.S. patent, Ser. No. 589,016 filed on Sep. 27, 1990), useful, inter alia, in ascertaining the efficacy of the ketone, alcohol and schiff base as repellents for the insect species named herein, indicating in schematic block flow diagram form the utilization of computer-assisted efficacy measuring apparatus.

FIG. 24 is an exploded view of a prior art olfactometer apparatus useful in determining the efficacy of the alcohol, ketone and schiff base of our invention, as a house fly (*Musca domestica* L. (Diptera Muscidae)) or mosquito (*Aedes aegypti*) repelling material. The air supply source 2634 feeds air through line 2634a to mixing station 2636. Treatment agent from source 2635 (e.g., such as the KOAVOL DH ®, KOAVONE ® or LYRAME ® to be tested as a house fly or mosquito repellent agent) is fed through line 2635a to mixing station 2636. At mixing station 2636, the air is mixed with the treatment agent such as the KOAVOL DH ®. The resulting air-treatment agent mixture (in the gas phase) is fed through a plurality (if desired) of lines e.g., 2636a and 2636g into portals at the side of the apparatus along a directional vector parallel to the surface of the base plate 2625 just above the said base plate 2625 and just below insect repellent quantitative detecting mean grids 2610. The base plate 2625 is separated from the spacer plate 2629 whereby the air-treatment agent lines 2636a, 2636g, et seq. are held in place using spacer ring 2628. Air and treatment agent in the gas phase exits through line 2633a using exhaust fan 2633 to the environment 2537. The air exit is indicated by reference numeral 2537.

Simultaneously, with the supplying of air and treatment agent from air supply source 2634 and treatment agent source 2635, light is supplied from above the enclosed insect feeding and/or stimulating means (collectively denoted as "IFS" means) through light guides 2652 from light source 2551 which is powered by electric power supply 2550. An example of such light guide is marketed by RADIO SHACK ® division of TANDY Corporation of Fort Worth, Tex. 76102 under the trademark ARCHER ®, Catalog No. 276-228 ("1.0 mm optical plastic fiber length 5 meters"). An example of light source 2551 is KRATOS Monochromatic Illuminator GM 100 Miniature VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. Another light supply source is the KRATOS GM 200 Double Grating Monochromator. Another example of a useful light source is the KRATOS GM 252 High Intensity Grating Monochromator.

The base plate 2625 is also separated from the spacer plate 2629 for the light guides 2652 whereby the light guides 2652 are held in place. In FIG. 24, spacer ring 2628 separates plate 2629 which holds the light guides 2652 in place from plate 2625 on which landing pads 2680 are located.

The olfactometer of FIG. 24 (which is also disclosed and claimed in application for U.S. patent, Ser. No. 589,016 filed on Sep. 27, 1990, the specification for which is incorporated by reference herein) is assisted with computer apparatus shown in schematic and block flow diagram form using reference numerals 2520, 2521, 2523 2524 and 2529. Dampers 2611 hold base plate 2625 in place horizontally. When an insect lands on landing site 2680, the landing is recorded electrically through sensor 2610. The sensor causes an electrical impulse caused by the pressure of the insect's landing to proceed through wire 2619a, 2619b, et seq. held in position by holder 2512 to a multi channel A.C. converter 2523 (using electric power supply 2539). Converter 2523 is associated with program tape storage 2524, printer 2520 and data link to digital computer 2521. Thus, a recording of the data as set forth in Tables I, II, supra and Tables VII and VIII infra is effected.

Figure 22:
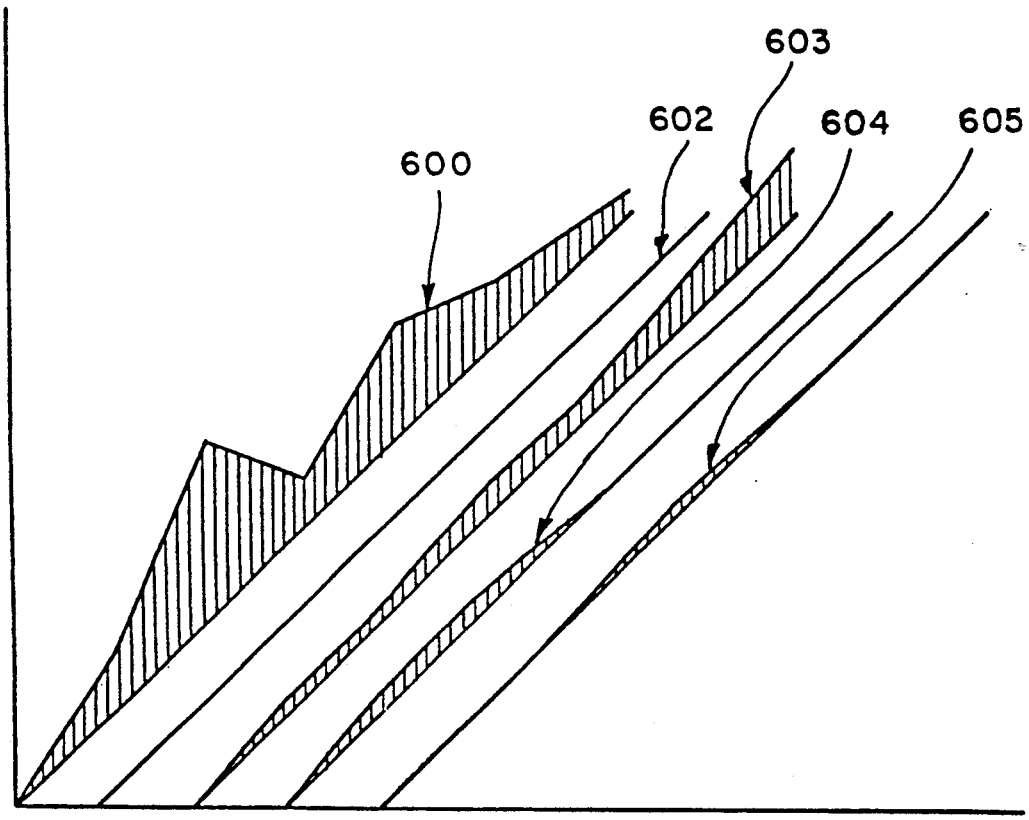
FIG. 22 is a series of graphs depicting in three dimensions (in the rectangular mode for the "x" and "y" axes) showing the relative repellency of LYRAME®, KOAVOL DH®, and KOAVONE®, as well as the attractiveness of air. The graphs are based on experiments run for a total of one hour with six intervals of 10 minutes each. The results are tabulated in Tables I and VII, infra. This series of graphs are for the attractiveness or repellency as against houseflies (*Musca domestica* L. (Diptera Muscidae)).
Figure 23:
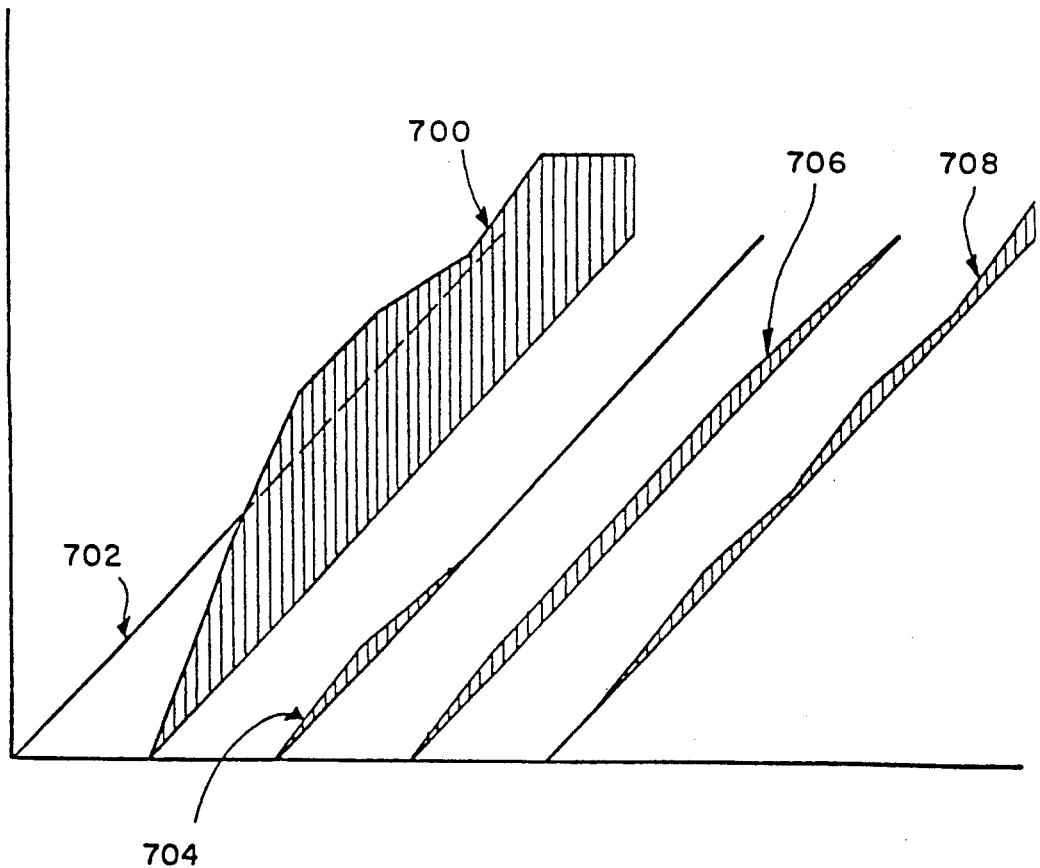
FIG. 23 is a series of graphs depicted in three dimensions (in a rectangular mode for the "x" and "y" axes) showing the relative attractiveness or repellency air, LYRAME®, KOAVOL DH®, and KOAVONE® for or against *Aedes aegypti*. The graphs are based on experiments run for a period of one hour with six intervals of 10 minutes each. The results are tabulated in TABLES II (supra) and VIII (infra).

FIGS. 22 and 23 are a series of graphs depicting in three dimensions (in a rectangular mode for the "x" and the "y" axes) showing the relative attractiveness or repellency of LYRAME ®, KOAVOL DH ® and KOAVONE ®, as well as air per se. The graphs are based on experiments run for a period of one hour with six intervals of 10 minutes each.

Thus, referring to FIG. 22, FIG. 22 shows relative repellency against house flies (*Musca domestica* L. (Diptera Muscidae)) of KOAVONE ® (the graph indicated by reference numeral 605), LYRAME ® (the graphs indicated by reference numerals 602 and 604), and KOAVOL DH ® (the graph indicated by reference numeral 603, as compared to the attractiveness of air itself (the graph for which is indicated by reference numeral 600.

The data supporting the graph of FIG. 22 is set forth in Table II and in the following Table VIII.

TABLE VIII

| Composition Tested | Reference Numeral for Graph | MUSCA DOMESTICA L. (DIPTERA MUSCIDAE) INSECTS PER INTERVAL | | | | | | |
|---|---|---|---|---|---|---|---|---|
| LYRAME ® | 604 | 0 | 46 | 55 | 12 | 12 | 13 | 3 |
| LYRAME ® | 602 | 0 | 3 | 4 | 0 | 1 | 0 | 0 |
| KOAVONE ® | 605 | 0 | 0 | 2 | 13 | 3 | 1 | 1 |
| KOAVOL DH ® | 603 | 0 | 16 | 16 | 26 | 15 | 41 | 52 |
| AIR | 600 | 0 | 153 | 463 | 133 | 293 | 167 | 94 |

Referring to FIG. 23, FIG. 23 shows the relative repellency of KOAVONE ®, KOAVOL DH ® and LYRAME ® with reference to clean air (as an "attractant" against the species of mosquito (*Aedes aegypti*). Thus the repellency against *Aedes aegypti* of KOAVONE ® is shown in the graph indicated by reference numeral 708. The repellency against *Aedes aegypti* of KOAVOL DH ® is shown by the graph indicated by reference numeral 706. The repellency against *Aedes aegypti* of LYRAME ® is shown by the graphs 704 and 702. The attractancy for *Aedes aegypti* of clean air (relative humidity 75-80%) is shown by the graph indicated by reference numeral 700. The data supporting the graphs set forth in FIG. 23 are set forth in the following Table VII.

TABLE VII

| Composition Tested | Reference Numeral for Graph | AEDES AEGYPTI INSECTS PER INTERVAL | | | | | | |
|---|---|---|---|---|---|---|---|---|
| LYRAME ® | 702 | 0 | 12 | 3 | 2 | 0 | 0 | 1 |
| LYRAME ® | 704 | 0 | 34 | 0 | 0 | 0 | 0 | 0 |
| KOAVONE ® | 708 | 0 | 12 | 67 | 26 | 80 | 30 | 85 |
| KOAVOL DH ® | 706 | 0 | 62 | 69 | 91 | 87 | 47 | 3 |
| AIR | 700 | 0 | 233 | 382 | 376 | 295 | 331 | 151 |

EXAMPLE I

Paraffin Wax Candle Body

| INGREDIENTS | PARTS BY WEIGHT |
|---|---|
| Paraffin wax | 95.0 |
| KOAVOL DH ® having the structure: | 5.0 |

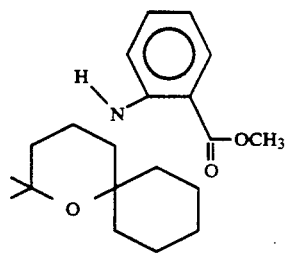

prepared according to
U.S. Pat. No. 4,517,990

The paraffin wax is intimately admixed at 150° C. and 10 atmospheres pressure with the KOAVOL DH ® in an autoclave with intensive shaking. The autoclave pressure is maintained with a nitrogen atmosphere. At the end of the period of 1 hour the autoclave is depressurized, the autoclave is opened and the resulting mixture is poured into cylindrical candle molds containing wicks.

The resulting candles on use evolve an aesthetically pleasing aroma and, in addition, give rise to efficacious house fly repellency. The candles are effective in preventing house flies from entering a room in which one candle is burning for a period of 10 minutes, the said room having dimensions of 6'×15'×15' having a 3'×3' open portal adjacent to a house fly-infested region in the month of August in Highlands, N.J., next to a very swampy area.

EXAMPLE II

A transparent candle base is produced by intimately admixing the following ingredients:

| INGREDIENTS | PARTS BY WEIGHT |
|---|---|
| VERSAMID ® 1635 | 34.0 |
| Barlol 12C2 | 51.0 |
| Butyl Stearate | 3.5 |
| NEVEX ® 100 | 5.0 |
| SPAN ® 60 | 1.5 |
| Isopropyl Isostearate | 4.0 |
| Isopropyl Myristate | 4.0 |

The foregoing mixture is placed in an autoclave and intimately admixed with a perfume-scent repellent composition containing LYRAME ®, a mixture of compounds having the structures:

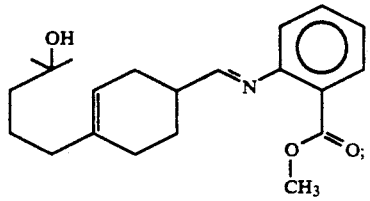

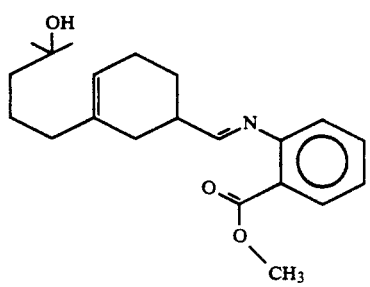

and prepared according to U.S. Pat. No. 4,775,720, the specification for which is incorporated herein at the rate of 8% by weight of the total candle base composition.

The autoclave is sealed and heated to 180° C. under 15 atmospheres pressure and maintained with vigorous shaking for a period of 5 hours. At the end of the 5 hour period the autoclave is depressurized (being under a nitrogen pressure atmosphere) and the autoclave is opened and the contents are then poured into cyclindrical candle molds four inches in height and two inches in diameter containing 0.125" wicks. The resulting candles have efficacious insect repellencies and have aesthetically pleasing aromas on use.

The candles are effective in preventing the following insects:

(a) *Musca domestica* L. (Diptera Muscidae);
(b) *Aedes aegypti;*
(c) *Aedes albopictus;*
(d) Anopheles spp.;
(e) *Coquillettidia perturbans;*
(f) Culiseta spp.;
(g) Culex spp.;
(h) Psorophora spp.;
(i) Culicoides spp.; and/or (j) *Lutzomyia* spp.

from entering a room in which two candles have been burning for 15 minutes, the said room having dimensions of 6'×15'×15' and having a 3'×3' open portal adjacent a house fly and mosquito infested region in Highlands, N.J., in the month of August in the temperate zone.

EXAMPLE III

The following candle base composition of matter is prepared:

| INGREDIENTS | PARTS BY WEIGHT |
|---|---|
| Polyamide (VERSAMID ® 940 manufactured by the Henkel Chemical Corporation of Minneapolis, Minnesota) | 30.0 |
| Stearic acid | 5.0 |
| Methyl-12-hydroxy stearate | 5.0 |
| 10 Carbon primary alcohol manufactured by the (Continental Oil Company; ALFOL ® 10); (ALFOL ® is a trademark of Conoco Division of E. I. DuPont of Wimington, Delaware | 5.0 |
| Myristyl Myristate | 10.0 |
| Stearic hydrazide | 0.1 |
| KOAVONE ® a mixture of compounds defined according to the structures: | 4.0 |

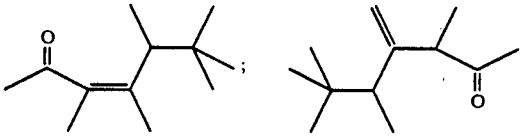

prepared according to U.S. Pat. No. 4,380,674 the specification for which is incorporated by reference herein

| Light white mineral oil | q.s to 100% |

All of the materials except the polyamide are mixed at room temperature. The mixture is then heated gradually with gradual addition of the polyamide and with agitation beginning with the commencement of addition of the polyamide. In the proportion required, the polyamide does not become fully soluble until the mixture reaches the temperature of about 220° F. The temperature on the order of 220° F. to 230° F. is maintained at atmospheric pressure with continued agitation until the polyamide is fully dissolved. Since higher temperatures promote solution of the polyamide this temperature range can be slightly exceeded with some advantage. As soon as the polyamide has dissolved completely, the mixture is poured into molds following the conventional practice in the manufacture of molded candles. As the candles cool they harden. The candles are then freed from the molds and tested for insect repellency.

The candles are effective in preventing the following insects from entering a room in which two candles have been burning for 15 minutes, the said room having dimensions of 6'×15'×15' and having a 3'×3' open portal adjacent to an insect infested region in the month of August in Highlands, N.J.:

(a) *Musca domestica* L. (Diptera Muscidae);
(b) *Aedes aegypti;*
(c) *Aedes albopictus;*
(d) *Anopheles* spp.;
(e) *Coquillettidia perturbans;*
(f) *Culiseta* spp.;
(g) *Culex* spp.;
(h) *Psorophora* spp.;
(i) *Culicoides* spp.; and/or
(j) *Lutzomyia* spp.

EXAMPLE IV

A study was conducted to evaluate the efficacy of candles which are designated "A", "B", and "C" in repelling house flies (*Musca domestica* L. Diptera Muscidae)).

Candle "A" contained 95% Paraffin Wax and 5% of the following composition:

100 parts by weight of KOAVOL DH ®; and
700 parts by weight of a perfume composition containing the following ingredients:

| INGREDIENTS | PARTS BY WEIGHT |
|---|---|
| (i) Perfume mixture of essential grams oils and chemicals, to with the methyl ester of 2,5-dihydroxy-4-6-dimethyl benzoic acid; dihydro myrcenol; oakmoss absolute; benzyl acetate; geraniol; isobornyl acetate; citronellyl acetate; para-t-butyl phenyl isovaleraldehyde; benzyl slicylate; hexyl cinnamic aldehyde; geranonitrile; patchouli oil; alpha-terpineol; tetrahydromuguol; phenyl ethyl alcohol; cedrenal; methyl ionone; cinnamyl acetate; benzyl benzoate; | 83.8 |
| (ii) Solvent: the methyl ester of dihydroabietic acid | 4.00 |

Candle "B" contained 90% Paraffin Wax and 10% cintronella oil.

Candle "C" contained only Paraffin Wax.

The candles are allowed to burn for 20 minutes and the number of house files repelled from a house fly-infested room is recorded for the next 60 minutes with the following equipment and procedure:

Materials

Test Chamber

The evaluation was conducted in a 28.3 cubic meter chamber with airing ports. A screened cage measuring 15 cm×15 cm×47.5 cm was attached inside an upper airing port, and a screened repellency observation cage measuring 15 cm×15 cm×32.5 cm was attached outside the upper airing port. The two cages were held together by a Masonite plate which fit firmly in the airing port. A 4-cm hole located in the center of each Masonite plate provided an escape for the test insects. A barrier was used to close the hole.

Attractant

A caged mouse was used as an attractant and was placed inside the chamber in the larger section of the repellency cage.

Test Insect

Adult house flies (*Musca domestica*) are test insects.

Procedure

For each replicate, 75 to 100 adult house flies were removed from the rearing cage by means of a vacuum aspirator, and transferred by carbon dioxide anesthesia to the inner cage containing the mouse. The assembled cage was placed in one of the upper ventilation ports of the chamber.

For each experimental situation the test insects were transferred to a clean cage containing the mouse. A house fly candle was placed centrally on the chamber floor and burned for 20 minutes before initiating the repellency counts. The maximum period for the repellency counts was 60 minutes. The first repellency count was made at 10 minutes after the burning ended, and subsequent counts were taken at 5-minute intervals thereafter. The number of house flies repelled were those escaping to the outside cage. For the control counts were made in a similar manner, but no candle was burned.

The same three candles were used for all four replicates. Between replicates the chamber was exhausted, the Kraft paper flooring for the chamber was replaced, and the two screened repellency cages were submerged in hot detergent water, rinsed and dried.

Results

The average percent of house flies repelled for each 5-minute exposure period through 60 minutes is reported in the following Table IX:

TABLE IX

| Sample | Replicate | Number of House Flies | \multicolumn{11}{c}{Cumulative Number of House Flies Repelled at Indicated Minutes} | Overall Percent |
|---|---|---|---|---|---|---|---|---|---|---|---|---|---|---|
| | | | 10 | 15 | 20 | 25 | 30 | 35 | 40 | 45 | 50 | 55 | 60 | |
| Untreated | 1 | 93 | 1 | 1 | 1 | 1 | 1 | 2 | 2 | 3 | 3 | 4 | 6 | 6.45 |
| (no candle | 2 | 67 | 0 | 1 | 2 | 3 | 5 | 6 | 6 | 6 | 6 | 7 | 7 | 10.45 |
| used) | 3 | 86 | 2 | 2 | 2 | 3 | 4 | 6 | 6 | 7 | 7 | 7 | 7 | 8.14 |
| | 4 | 90 | 2 | 3 | 3 | 3 | 3 | 4 | 5 | 5 | 5 | 5 | 5 | 5.56 |
| Total | | 336 | 5 | 7 | 8 | 10 | 13 | 17 | 19 | 21 | 21 | 23 | 25 | |
| Average Percent | | | 1 | 2 | 2 | 3 | 4 | 5 | 6 | 6 | 6 | 7 | 7 | 7.44 |
| A | 1 | 108 | 2 | 5 | 7 | 8 | 8 | 8 | 8 | 10 | 10 | 10 | 12 | 11.11 |
| | 2 | 95 | 0 | 5 | 5 | 6 | 7 | 7 | 9 | 11 | 12 | 12 | 16 | 16.84 |
| | 3 | 86 | 3 | 6 | 8 | 8 | 10 | 10 | 11 | 11 | 12 | 12 | 13 | 15.12 |
| | 4 | 96 | 2 | 3 | 5 | 6 | 9 | 11 | 11 | 14 | 16 | 17 | 17 | 17.71 |
| Total | | 385 | 7 | 19 | 25 | 28 | 34 | 36 | 39 | 46 | 50 | 51 | 58 | |
| Average Percent | | | 2 | 5 | 6 | 7 | 9 | 9 | 10 | 12 | 13 | 13 | 15 | 15.06 |
| B | 1 | 80 | 4 | 5 | 7 | 7 | 8 | 8 | 9 | 9 | 9 | 10 | 11 | 13.75 |
| | 2 | 100 | 2 | 4 | 5 | 6 | 7 | 10 | 11 | 11 | 11 | 12 | 12 | 12.00 |
| | 3 | 87 | 2 | 2 | 3 | 4 | 5 | 5 | 6 | 6 | 6 | 6 | 7 | 8.04 |
| | 4 | 91 | 2 | 4 | 5 | 6 | 6 | 6 | 7 | 7 | 7 | 9 | 10 | 10.99 |
| Total | | 358 | 10 | 15 | 20 | 23 | 26 | 29 | 33 | 33 | 33 | 37 | 41 | |
| Average Percent | | | 3 | 4 | 6 | 6 | 7 | 8 | 9 | 9 | 9 | 10 | 11 | 11.45 |
| C | 1 | 79 | 6 | 8 | 8 | 8 | 8 | 8 | 8 | 8 | 8 | 9 | 10 | 12.66 |
| | 2 | 86 | 3 | 5 | 5 | 6 | 6 | 6 | 6 | 6 | 7 | 7 | 8 | 9.30 |
| | 3 | 92 | 2 | 4 | 4 | 5 | 7 | 7 | 7 | 7 | 7 | 7 | 8 | 8.70 |
| | 4 | 91 | 0 | 1 | 1 | 2 | 2 | 2 | 4 | 6 | 7 | 7 | 9 | 9.89 |
| Total | | 348 | 11 | 18 | 18 | 11 | 23 | 23 | 25 | 27 | 29 | 30 | 35 | |
| Average Percent | | | 3 | 5 | 5 | 6 | 7 | 7 | 7 | 8 | 8 | 9 | 10 | 10.06 |

The results of this experiment show that the candle containing the KOAVONE ® composition (2.5% of the total weight) is about 40% more efficacious from an insect repellency standpoint than a candle containing 10% citronella oil . . . and in addition, such candles containing the KOAVONE ® composition on burning yield an aesthetically pleasing scent which is totally unlike the 10% citronella oil containing candle which yields an aesthetically displeasing scent.

What is claimed is:

1. A process for repelling insects selected from the group consisting of house files and mosquitoes from a user of soap comprising the steps of:
   (i) forming an insect repelling soap consisting essentially of a soap base and in intimate contact therewith an insect repellent quantity and concentration of an insect repellent composition of matter which is a mixture of compounds having the structures:

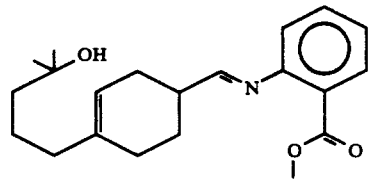

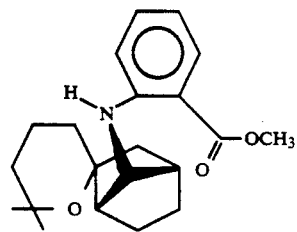

and

-continued
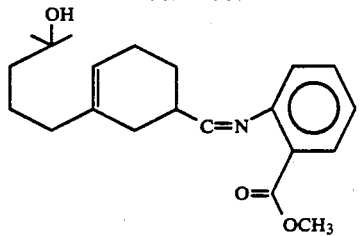
and
(ii) applying said insect repelling soap to a user of said insect repelling soap in a sufficient quantity to repel insects from said user.
* * * * *